US012643862B2

(12) United States Patent
Wuerthner et al.

(10) Patent No.: US 12,643,862 B2
(45) Date of Patent: Jun. 2, 2026

(54) RYLENE DICARBOXIMIDES

(71) Applicant: BASF SE, Ludwigshafen am Rhein (DE)

(72) Inventors: Frank Wuerthner, Höchberg (DE); Magnus Mahl, Wuerzburg (DE); Helmut Reichelt, Ludwigshafen am Rhein (DE)

(73) Assignee: BASF SE, Ludwigshafen am Rhein (DE)

(*) Notice: Subject to any disclaimer, the term of this patent is extended or adjusted under 35 U.S.C. 154(b) by 971 days.

(21) Appl. No.: 17/795,280

(22) PCT Filed: Jan. 27, 2021

(86) PCT No.: PCT/EP2021/051836
§ 371 (c)(1),
(2) Date: Jul. 26, 2022

(87) PCT Pub. No.: WO2021/151928
PCT Pub. Date: Aug. 5, 2021

(65) Prior Publication Data

US 2023/0097455 A1 Mar. 30, 2023

(30) Foreign Application Priority Data

Jan. 29, 2020 (EP) .................................... 20154406

(51) Int. Cl.

*C07D 221/18* (2006.01)
*C09D 5/22* (2006.01)
*C09K 11/06* (2006.01)
*H10H 20/851* (2025.01)

(52) U.S. Cl.

CPC ............. *C07D 221/18* (2013.01); *C09D 5/22* (2013.01); *C09K 11/06* (2013.01); *C09K 2211/1029* (2013.01); *H10H 20/8512* (2025.01)

(58) Field of Classification Search

CPC ........ C07D 221/18; C09D 5/22; C09K 11/06; C09K 2211/1029; H10H 20/8512
See application file for complete search history.

(56) References Cited

U.S. PATENT DOCUMENTS

2008/0241492 A1 10/2008 Demartin et al.
2009/0124732 A1 5/2009 Konemann et al.

FOREIGN PATENT DOCUMENTS

DE 102004018547 A1 2/2005
DE 102004057585 A1 6/2006
WO 96/22332 A1 7/1996
WO 97/22607 A1 6/1997
WO 2002/076988 A2 10/2002

(Continued)

OTHER PUBLICATIONS

Ayyappanpillai Ajayaghosh, "Chemistry of squaraine-derived materials: near-IR dyes, low band gap systems, and cation sensors.", Accounts of Chemical Research, vol. 38, Issue 6, Apr. 8, 2005, pp. 449-459.

(Continued)

*Primary Examiner* — Renee Claytor
*Assistant Examiner* — Christopher Lindsay Johnson
(74) *Attorney, Agent, or Firm* — Faegre Drinker Biddle & Reath LLP

(57) ABSTRACT

The present invention relates to compounds of the formula (I), a process for its preparation and its use as fluorescent dye that absorbs light emitted from an irradiation source and emits light different from that of the irradiation source and having a wavelength in the range from 680 to 950 nm; in photovoltaic applications; or as semiconductor in organic electronic applications; as laser dye, in an ink for machine readability and/or security applications or for the laser-welding of plastics; or for brand protection or as marker for liquids. The compounds of formula (I) may have a high fluorescence quantum yield, a high molar extinction coefficient, a high solubility and stability in the application medium, good storage stability and/or good detectability even in very small amounts in the correspondingly marked liquids.

(I)

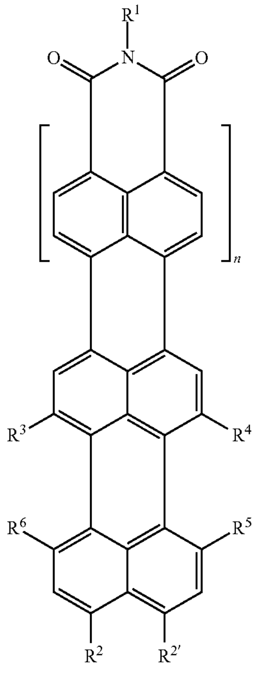

10 Claims, 3 Drawing Sheets

(56) References Cited

FOREIGN PATENT DOCUMENTS

| | | | |
|---|---|---|---|
| WO | 2002/077081 | A1 | 10/2002 |
| WO | 2003/104232 | A1 | 12/2003 |
| WO | 2004/005427 | A2 | 1/2004 |
| WO | 2007/006717 | A1 | 1/2007 |
| WO | 2007/099059 | A1 | 9/2007 |
| WO | 2018/096083 | A1 | 5/2018 |

OTHER PUBLICATIONS

European Search Report for EP Patent Application No. 20154406.1, Issued on Jul. 6, 2020, 9 pages.

Feng, et al., "Synthesis and application of rylene imide dyes as organic semiconducting materials", Chemistry—An Asian Journal, vol. 13, Issue 1, Nov. 16, 2017, pp. 20-30.

Frank Würthner, "Perylene bisimide dyes as versatile building blocks for functional supramolecular architectures", Chemical communications, vol. 14, May 12, 2004, pp. 1564-1579.

Ilina, et al., "Squaraine dyes: molecular design for different applications and remaining challenges", Bioconjugate chemistry, vol. 31, Issue 2, Jul. 31, 2019, pp. 194-213.

Koch, et al., "Polyarylenes and Poly (arylenevinylene) s, V. Synthesis of Tetraalkyl-Substituted Oligo (1,4-naphthylene) s and Cyclization to Soluble Oligo (peri-naphthylene) s2", Chemische Berichte, vol. 124, Issue 9, Sep. 1991, pp. 2091-2100.

Lee, et al., "Electrochemistry, spectroscopy and electrogenerated chemiluminescence of perylene, terrylene, and quaterrylene diimides in aprotic solution", Journal of the American Chemical Society, vol. 121, Issue 14, Mar. 26, 1999, pp. 3513-3520.

Liu, et al., "A Water-Soluble, NIR-Absorbing Quaterrylenediimide Chromophore for Photoacoustic Imaging and Efficient Photothermal Cancer Therapy", Angewandte Chemie International Edition, vol. 58, Issue 6, Dec. 7, 2018, pp. 1638-1642.

Loudet, et al., "BODIPY dyes and their derivatives: syntheses and spectroscopic properties", Chemical reviews, vol. 107, Issue 11, Oct. 9, 2007, pp. 4891-4932.

Mahl, et al., "Tetrachlorinated Polycyclic Aromatic Dicarboximides: New Electron-Poor p. Scaffolds and NIR Emitters by Palladium-Catalyzed Annulation Reaction", Chemistry—A European Journal, vol. 24, Issue 37, Apr. 24, 2018, pp. 9409-9416.

Osswald, et al., "Effects of bay substituents on the racemization barriers of perylene bisimides: resolution of atropo-enantiomers", Journal of the American Chemical Society, vol. 129, Issue 46, Oct. 27, 2007, p. 14319-14326.

Pagoaga, et al., "Synthesis and Characterisation of 1, 7-Di-and Inherently Chiral 1, 12-Di-and 1, 6, 7, 12-Tetraarylperylenetetracarbox-3, 4: 9, 10-diimides", European Journal of Organic Chemistry, vol. 2014, Issue 24, Jul. 15, 2014, pp. 5178-5195.

Qiu, et al., "Suzuki coupling reaction of 1, 6, 7, 12-tetrabromoperylene bisimide", Organic letters, vol. 8, Issue 5, Feb. 7, 2006, pp. 867-870.

Quante, et al., "Quaterrylenebis (dicarboximides)", Angewandte Chemie International Edition in English, vol. 34, Issue 12, Jul. 7, 1995, pp. 1323-1325.

Queste, et al., "Synthesis and characterization of 1, 7-disubstituted and 1, 6, 7, 12-tetrasubstituted perylenetetracarboxy-3, 4: 9, 10-diimide derivatives", New Journal of Chemistry, vol. 34, Issue 11, Jun. 11, 2010, pp. 2537-2545.

Ulrich, et al., "The chemistry of fluorescent bodipy dyes: versatility unsurpassed", Angewandte Chemie International Edition, vol. 47, Issue 7, Jan. 25, 2008, pp. 1184-1201.

Weil, et al., "The rylene colorant family-tailored nanoemitters for photonics research and applications", Angewandte Chemie International Edition, vol. 49, Issue 48, Oct. 25, 2010, pp. 9068-9093.

Wurthner, et al., "Perylene bisimide dye assemblies as archetype functional supramolecular materials", Chemical reviews, vol. 116, Issue 3, Aug. 13, 2015, pp. 962-1052.

Chen et al., "Beyond perylene diimides: synthesis, assembly and function of higher rylene chromophores," Journal of Materials Chemistry C, vol. 2, vol. 11, Jan. 2014, pp. 1938-1956.

Geerts et al., "Quaterrylenebis(Dicarboximide)S: Near Infrared Absorbing and Emitting Dyes," Journal of Materials Chemistry, vol. 8, No. 11, Nov. 1, 1998, pp. 2357-2369.

Holtrup et al., "Terrylenimides : New NIR Fluorescent Dyes", Chem. Eur. J., Vol. (3), No. 2, 1997, pp. 219-225.

International Preliminary Report on Patentability received for PCT Patent Application No. PCT/EP2021/051836, mailed on Aug. 11, 2022, 9 pages.

International Search Report and Written Opinion received for PCT Patent Application No. PCT/EP2021/051836, mailed on Feb. 26, 2021, 12 pages.

Zagranyarski et al., "Toward Perylene Dyes by the Hundsdiecker Reaction," Organic Letters, vol. 16, No. 11, May 16, 2014, pp. 2814-2817.

RYLENE DICARBOXIMIDES

CROSS-REFERENCE TO RELATED APPLICATIONS

This application is a national stage application (under 35 U.S.C. § 371) of PCT/EP2021/051836, filed Jan. 27, 2021, which claims benefit of European Application No. 20154406.1, filed Jan. 29, 2020, both of which are incorporated herein by reference in their entirety.

DESCRIPTION

The present invention relates to compounds of the formula (I)

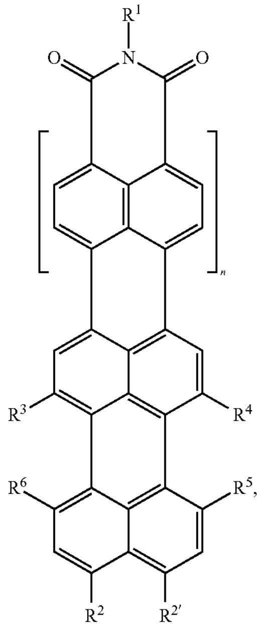

a process for its preparation and its use as fluorescent dye that absorbs light emitted from an irradiation source and emits light different from that of the irradiation source and having a wavelength in the range from 680 to 950 nm; in photovoltaic applications; or as semiconductor in organic electronic applications; as laser dye, in an ink for machine readability and/or security applications or for the laser-welding of plastics; or for brand protection or as marker for liquids. The compounds of formula (I) may have a high fluorescence quantum yield, a high molar extinction coefficient, a high solubility and stability in the application medium, good storage stability and/or good detectability even in very small amounts in the correspondingly marked liquids.

TECHNICAL BACKGROUND

Rylene dicarboximides constitute a most prominent class of pigments and dyes due to their extraordinary properties: excellent chemical, thermal and photo stability as well as strong and tunable absorption and fluorescence. Thus, they find use in a broad variety of applications (F. Würthner, Chem. Commun. 2004, 1564-1579 [1]; T. Weil, T. Vosch, J. Hofkens, K. Peneva, K. Müllen, Angew. Chem. Int. Ed. 2010, 49, 9068-9093 [2]; L. Chen, C. Li, K. Müllen, J. Mater. Chem. C 2014, 2, 1938-1956 [3]; F. Würthner, C. R. Saha-Möller, B. Fimmel, S. Ogi, P. Leowanawat, D. Schmidt, Chem. Rev. 2016, 116, 962-1052 [4]; J. Feng, W. Jiang, Z. Wang, Chem. Asian J. 2018, 13, 20-30 [5]).

While perylene bis(dicarboximides)—the most well-studied rylene dye class—reache fluorescence quantum yields up to unity, the longitudinal extended terrylene imides have already decreased fluorescence quantum yields, while the absorbance and the fluorescence is bathochromically shifted due to the π=extension ([3], F. O. Holtrup, G. R. J. Müller, H. Quante, S. Defeyter, F. C. DeSchryver, K. Müllen, Chem. Eur. J. 1997, 3, 219-225 [6]). The next congener, quaterrylene imides, show more red-shifted absorption and emission in the NIR spectral region, however, with almost diminished fluorescence quantum yields (H. Quante, K. Müllen, Angew. Chem. Int. Ed. 1995, 34, 1323-1325 [7]; Y. Geerts, H. Quante, H. Platz, R. Mahrt, M. Hopmeier, A. Böhm, K. Müllen, J. Mater. Chem. 1998, 8, 2357-2369 [8]). Thus, these dyes are despite of the excellent thermal and chemical robustness and light fastness not useful for fluorescence applications and other classes of dyes have to be applied for applications that rely on fluorescence. Unfortunately, all other classes of dyes which show an enhanced emission in the NIR region, like BODIPY (A. Loudet, K. Burgess, Chem. Rev. 2007, 107, 4891-4932 [9], G. Ulrich, R. Ziessel, A. Harriman, Angew. Chem. Int. Ed. 2008, 47, 1184-1201 [10]) or squarine (A. Ajayaghosh, Acc. Chem. Res. 2005, 38, 449-459 [11], K. Ilina, W. M. MacCuaig, M. Laramie, J. N. Jeouty, L. R. McNally, M. Henary, Bioconjugate Chem. 2019, DOI: https//doi.or/10.1021/acs.bioconjchem.9b00482 [12]) dyes, suffer from lower stability. Therefore, the development of rylene-based dyes with an emission in the NIR region (>750 nm) and high fluorescence quantum yields is of high interest.

The synthesis of new π-extended, tetrachlorinated rylene dicarboximides, which displayed an emission in the NIR region was described in M. Mahl, K. Shoyama, J. Rühe, V. Grande, F. Würthner, Chem. Eur. J. 2018, 24, 9409-9416 [13].

Compared to their non-chlorinated counterparts these compounds show a distinct bathochromic shift in their absorption and emission spectra. This trend is similar by comparing non-chlorinated and bay-chlorinated perylene bis(dicarboximides). [1] An even more pronounced redshift is observed, when the bay-substituted chlorines at the perylene bis(dicarboximide) scaffold are substituted with aryl groups (W. F. Qiu, S. Y. Chen, X. B. Sun, Y. Q. Liu, D. B. Zhu, Org. Lett. 2006, 8, 867-870 [14]; M. Queste, C. Cadiou, B. Pagoaga, L. Giraudet, N. Hoffmann, New J. Chem. 2010, 34, 2537-2545 [15], B. Pagoaga, L. Giraudet, N. Hoffmann, Eur. J. Org. Chem. 2014, 5178-5195 [16]).

In addition, terrylene tetracarboximide compounds and its higher homologs are disclosed, for example, in WO96/22332, WO97/22607, WO02/76988, WO2003/104232, WO2007/006717 and WO2007/099059.

None of these documents describes dicarboximides compounds having the characteristic substituents attached at the skeleton as claimed in the present invention.

Thus, it is an object of the present invention to provide dicarboximides that have a high stability, high absorption coefficient and/or fluorescence quantum yield compared to compounds known in the art.

SUMMARY OF THE INVENTION

It was surprisingly found that these and further objectives are achieved by the compounds of formula (I) as defined herein below.

Thus, in a first aspect, the invention relates to a compound of the formula (I)

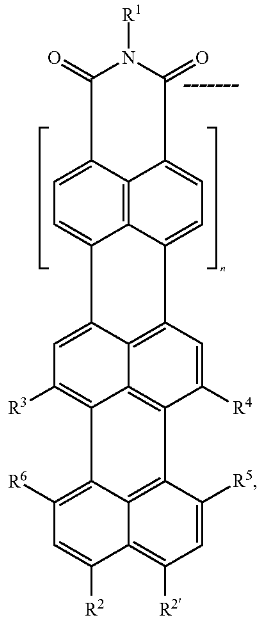

wherein n is 0 or 1;

$R^1$ is selected from the group consisting of hydrogen, $C_1$-$C_{24}$-alkyl, $C_1$-$C_{24}$-haloalkyl, $C_3$-$C_{24}$-cycloalkyl, $C_6$-$C_{10}$-aryl and $C_6$-$C_{10}$-aryl-$C_1$-$C_{10}$-alkylene, where the rings of cycloalkyl, aryl, and aryl-alkylene in the three last-mentioned radicals are unsubstituted or substituted with one or more substituents $R^7$, and where $C_1$-$C_{24}$-alkyl, $C_1$-$C_{24}$-haloalkyl and the alkylene moiety of $C_6$-$C_{10}$-aryl-$C_1$-$C_{10}$-alkylene may be interrupted by one or more heteroatoms or heteroatomic groups selected from O, S and $NR^8$;

$R^3$, $R^4$, $R^5$ and $R^6$, independently of each other, are selected from $C_6$-$C_{10}$-aryloxy, $C_2$-$C_{10}$-heteroaryl and $C_6$-$C_{10}$-aryl, wherein $C_6$-$C_{10}$-aryloxy is substituted by one or more identical or different substituents $R^7$; $C_2$-$C_{10}$-heteroaryl is unsubstituted or substituted by one or more identical or different substituents $R^7$ and $C_6$-$C_{10}$-aryl is substituted by one or more identical or different substituents $R^7$;

$R^2$ and $R^{2'}$ together form a group of formula (II)

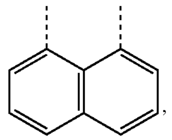

represents the bond to the rylene basic skeleton, the group of formula (II) is unsubstituted or substituted with one or more substituents $R^7$, or the group of formula (II) may be part of an annulated ring system, which is unsubstituted or substituted with one or more substituents $R^7$, or in case of the group of formula (II) two substituents $R^7$ may form a group

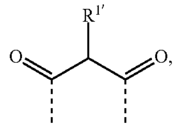

wherein represents the bond to the group of formula (II), $R^{1'}$ is selected from the group consisting of hydrogen, $C_1$-$C_{24}$-alkyl, $C_1$-$C_{24}$-haloalkyl, $C_3$-$C_{24}$-cycloalkyl, $C_6$-$C_{10}$-aryl and $C_6$-$C_{10}$-aryl-$C_1$-$C_{10}$-alkylene, where the rings of cycloalkyl, aryl, and aryl-alkylene in the three last-mentioned radicals are unsubstituted or substituted with one or more substituents $R^7$, and where $C_1$-$C_{24}$-alkyl, $C_1$-$C_{24}$-haloalkyl and the alkylene moiety of $C_6$-$C_{10}$-aryl-$C_1$-$C_{10}$-alkylene may be interrupted by one or more heteroatoms or heteroatomic groups selected from O, S and $NR^8$;

each $R^7$ is selected from $C_1$-$C_{24}$-alkyl, $C_1$-$C_{24}$-fluoroalkyl, $C_1$-$C_{24}$-alkoxy, fluorine, chlorine or bromine; and $R^8$ is hydrogen, $C_1$-$C_{20}$-alkyl, $C_3$-$C_{24}$-cycloalkyl, heterocycloalkyl, hetaryl or $C_6$-$C_{10}$-aryl.

A further aspect of the present invention relates to the use of the compound of formula (I) as defined above as fluorescent dye that absorbs light emitted from an irradiation source and emits light different from that of the irradiation source and having a wavelength in the range from 680 to 950 nm.

A further aspect of the present invention relates to the use of the compound of formula (I) as defined above as fluorescent dye in a converted LED.

A further aspect of the present invention relates to the use of the compound of formula (I) as defined above in a near infrared spectrometer apparatus.

A further aspect of the present invention relates to the use of the compound of formula (I) as defined above in an agricultural film.

A further aspect of the present invention relates to the use of the compound of formula (I) as defined above in photovoltaic applications.

A further aspect of the present invention relates to the use of the compound of formula (I) as defined above in a fluorescent solar concentrator.

A further aspect of the present invention relates to the use of the compound of formula (I) as defined above as semiconductor in organic electronic applications.

A further aspect of the present invention relates to the use of the compound of formula (I) as defined above as laser dye, in an ink for machine readability and/or security applications or for the laser-welding of plastics.

A further aspect of the present invention relates to the use of the compound of formula (I) as defined above for brand protection or as marker for liquids, especially oils.

A further aspect of the present invention relates to a color converter comprising (i) a compound of formula (I) as defined above;

(ii) a polymeric matrix material selected from a polystyrene, polycarbonate, polyacrylate, polymethylmethacrylate, polymethacrylate, polyvinylpyrrolidone, polyvinyl acetate, polyvinyl chloride, polybutene, silicone, epoxy resin, polyvinyl alcohol, poly(ethylene vinylalcohol)-copolymer, polyacrylonitrile, polyvinylidene chloride, polystyrene acrylonitrile, polybutylene terephthalate, polyethylene terephthalate, a 2,5-furandicarboxylate polyester, polyvinyl butyrate, polyvinyl chloride, polyamides, polyoxymethylenes, polyimides, polyetherimides or mixtures thereof; and (iii) optionally a light scattering agent.

A further aspect of the present invention relates to a near infrared light source, comprising (i) a light source, selected from a blue LED, red LED or white LED; and (ii) a color converter as defined above.

The compound of formula (I) as described herein provides several benefits, in particular high solubility and stability in the application medium. Moreover, certain compounds of formula (I) are outstandingly suitable as fluorescent dye so that they can be used as NIR compound emitting light comprising a wavelength of 680 to 950 nm due to their good solubility in the application medium and the high fluorescence quantum yield. In addition, the compound of formula (I) is outstandingly suitable as marker for liquids, especially oils, such as mineral oils due to its favorable application properties such as good solubility in the liquids, high molar extinction coefficient, good storage stability and good detectability even in very small amounts in the correspondingly marked liquids.

As another benefit, for sterically demanding substituents on the polyaromatic dicarboximide scaffold atropo-enantiomers are formed, which could be separated by HPLC and have a high racemization barrier. The combination of NIR absorption and NIR emission with stable chirality even at elevated temperature makes the newly reported dyes outstanding chiroptical molecular probes.

DETAILED DESCRIPTION OF THE INVENTION

Figure 1:
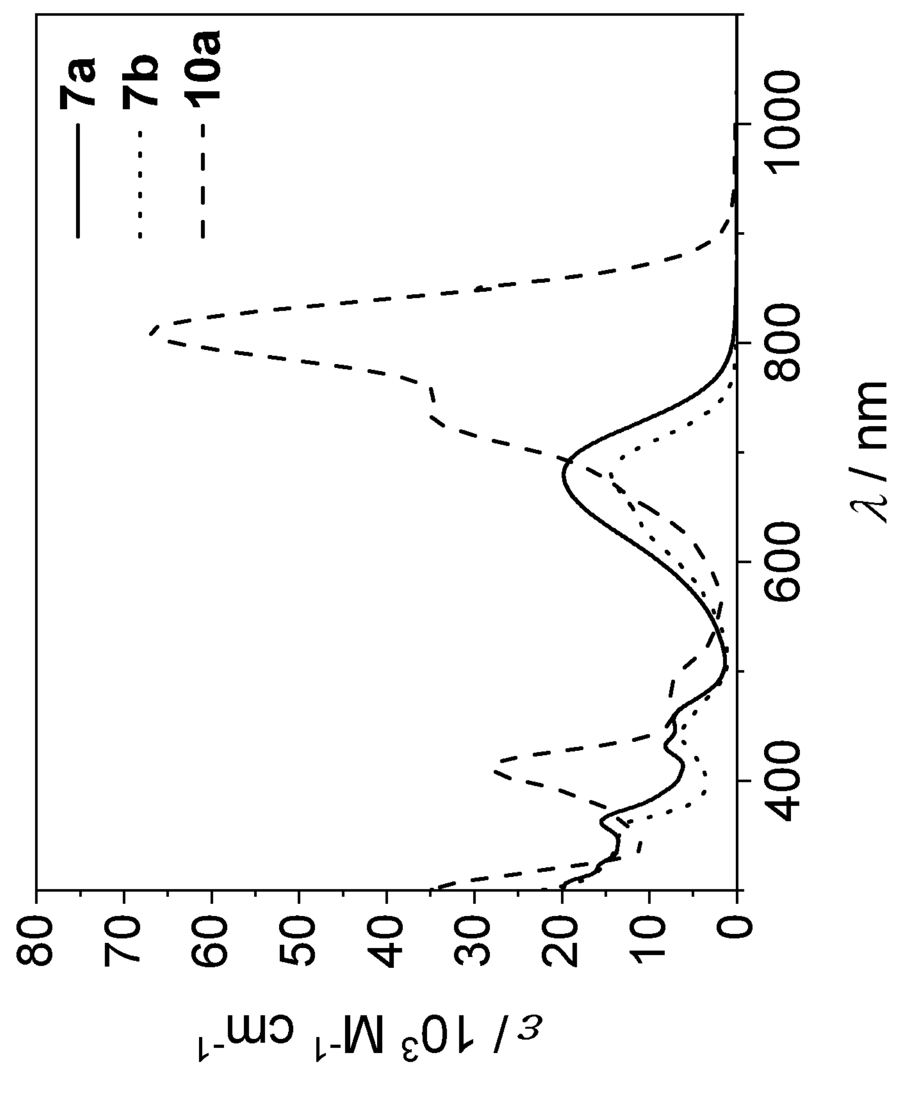
FIG. 1: UV/vis/NIR absorption spectra of 7a, 7b and 10a in dichloromethane solutions at room temperature.

In the context of the present invention, the term "fluorescence quantum yield (QY)" is defined as ratio of the number of photons emitted to the number of photons absorbed. Here and throughout the specification, the term "near-infrared light" denotes light that ranges from 680 to 1100 nm.

Here and throughout the specification, the term "visible light" denotes light that ranges from approximately 380 nm to 740 nm.

Here and throughout the specification, the term "halogen" denotes fluorine, bromine, chlorine or iodine, particularly chlorine, bromine or iodine.

Here and throughout the specification, the prefixes $C_n$-$C_m$ used in connection with compounds or molecular moieties each indicate a range for the number of possible carbon atoms that a molecular moiety or a compound can have.

The term "$C_1$-$C_n$-alkyl" denotes a group of linear or branched saturated hydrocarbon radicals having from 1 to n carbon atoms. For example, the term $C_1$-$C_{24}$-alkyl denominates a group of linear or branched saturated hydrocarbon radicals having from 1 to 24 carbon atoms, while the term $C_1$-$C_4$-alkyl denominates a group of linear or branched saturated hydrocarbon radicals having from 1 to 4 carbon atoms, the term $C_5$-$C_{20}$ alkyl denominates a group of linear or branched saturated hydrocarbon radicals having from 5 to 20 carbon atoms and the term $C_6$-$C_{20}$-alkyl denominates a group of linear or branched saturated hydrocarbon radicals having from 6 to 20 carbon atoms. Examples of alkyl include but are not limited to methyl, ethyl, n-propyl, isopropyl, n-butyl, sec-butyl, isobutyl, tert-butyl, 2-methylpropyl (isopropyl), 1,1-dimethylethyl (tert-butyl), pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, 1,1,3,3-tetramethylbutyl (tert-octyl), nonyl, isononyl, decyl, undecyl, dodecyl, tridecyl, isotridecyl, tetradecyl, pentadecyl, hexadecyl, heptadecyl, octadecyl, nonadecyl, eicosyl, heneicosyl docosyl and in case of nonyl, isononyl, decyl, undecyl, dodecyl, tridecyl, isotridecyl, tetradecyl, pentadecyl, hexadecyl, heptadecyl, octadecyl, nonadecyl, eicosyl, heneicosyl docosyl their isomers, in particular mixtures of isomers such as "isononyl", "isodecyl". Examples of $C_1$-$C_4$-alkyl are for example methyl, ethyl, propyl, 1-methylethyl, butyl, 1-methylpropyl, 2-methylpropyl or 1,1-dimethylethyl.

The term "$C_1$-$C_{24}$-haloalkyl" as used herein denotes straight-chain or branched $C_1$-$C_{24}$ alkyl as defined above, where some or all of the hydrogen atoms in these groups may be replaced by halogen atoms as mentioned above. Examples for $C_1$-$C_2$-haloalkyl are chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl.

The term "$C_1$-$C_{24}$-fluoroalkyl" as used herein denotes straight-chain or branched $C_1$-$C_{24}$ alkyl as defined above, where some or all of the hydrogen atoms in these groups may be replaced by fluorine above. Examples for $C_1$-$C_2$-fluoroalkyl are fluoromethyl, difluoromethyl, trifluoromethyl, 1-fluoroethyl, 2-fluoroethyl, 2,2-difluoroethyl, 2,2,2-trifluoroethyl and pentafluoroethyl.

The term "$C_1$-$C_{24}$-alkoxy" as used herein denotes straight-chain or branched $C_1$-$C_{24}$ alkyl as defined above bound to the remainder of the molecule through an oxygen. Examples for $C_1$-$C_4$-alkoxy are methoxy, ethoxy, n-propoxy, 1-methylethoxy, butoxy, 1-methylpropoxy, 2-methylpropoxy and 1,1-dimethylethoxy.

The term "$C_3$-$C_{24}$-cycloalkyl" as used herein denotes a mono-, bi- or tricyclic cycloalkyl radical which is unsubstituted or substituted by one or more radicals $R^7$, for example 1, 2, 3 or 4 $R^7$ radicals. Examples of $C_3$-$C_{24}$-cycloalkyl include but are not limited to cyclopropyl, cyclobutyl, cyclopentyl, cyclohexyl, methylcyclohexyl, dimethylcyclohexyl, cycloheptyl, cyclooctyl, cyclododecyl, cyclohexadecyl and norbornyl (=bicyclo[2.2.1]heptyl).

The term "heterocyclyl" as used herein refers to a mono- or bicyclic saturated or partially unsaturated ring system having 3, 4, 5, 6, 7 or 8 ring members ($C_3$-$C_8$-heterocyclyl), comprising besides carbon atoms as ring members, one, two, three or four heteroatoms or heteroatom-containing groups selected from O, N, S, SO and $S(O)_2$ as ring members.

The term "$C_6$-$C_{10}$-aryl" as used herein denotes phenyl or naphthyl.

The term "$C_6$-$C_{10}$-aryloxy" as used herein denotes phenoxy and naphthyloxy.

The term "alkylene" or "alkanediyl" as used herein denotes a straight-chain or branched alkyl radical as defined above, wherein one hydrogen atom at any position of the carbon backbone is replaced by one further binding site, thus forming a bivalent moiety.

The term "$C_6$-$C_{10}$-aryl-$C_1$-$C_{10}$-alkylene" (which may also be referred to as aralkyl) as used herein refers to $C_6$-$C_{10}$-aryl-substituted alkyl radicals having at least one unsubstituted or substituted aryl group, as defined herein. The alkyl group of the aralkyl radical may be interrupted by one or more nonadjacent groups selected from O, S and $NR^8$, wherein $R^8$ is as defined above. $C_6$-$C_{10}$-aryl-$C_1$-$C_{10}$-alkylene is preferably phenyl-$C_1$-$C_{10}$-alkylene, more preferably phenyl-$C_1$-$C_4$-alkylene, for example benzyl, 1-phenethyl, 2-phenethyl, 1-phenprop-1-yl, 2-phenprop-1-yl, 3-phenprop-1-yl, 1-phenbut-1-yl, 2-phenbut-1-yl, 3-phenbut-1-yl, 4-phenbut-1-yl, 1-phenbut-2-yl, 2-phenbut-2-yl, 3-phenbut-2-yl or 4-phenbut-2-yl; preferably benzyl and 2-phenethyl.

The term "hetaryl" or "heteroaryl" as used herein refers to heteroaromatic, monocyclic, bicyclic or tricyclic condensed system with 5, 6, 7, 8, 9, 10, 11, 12, 13 or 14 ring members in which at least one of the rings is aromatic and which contains 1, 2, 3 or 4 heteroatoms selected from N, S or O. Monocyclic hetaryl groups are preferably 5- or 6-membered hetaryl groups comprising 1, 2 or 3 heteroatoms selected from O, S or N such as 2-furyl (furan-2-yl), 3-furyl (furan-3-yl), 2-thienyl (thiophen-2-yl), 3-thienyl (thiophen-3-yl), 1H-pyrrol-2-yl, 1H-pyrrol-3-yl, pyrrol-1-yl, imidazol-2-yl, imidazol-1-yl, imidazol-4-yl, pyrazol-1-yl, pyrazol-3-yl, pyrazol-4-yl, pyrazol-5-yl, 3-isoxazolyl, 4-isoxazolyl, 5-isoxazolyl, 3-isothiazolyl, 4-isothiazolyl, 5-isothiazolyl, 2-oxazolyl, 4-oxazolyl, 5-oxazolyl, 2-thiazolyl, 4-thiazolyl, 5-thiazolyl, 1,2,4-oxadiazol-3-yl, 1,2,4-oxadiazol-5-yl, 1,3,4-oxadiazol-2-yl, 1,2,4-thiadiazol-3-yl, 1,2,4-thiadiazol-5-yl, 1,3,4-thiadiazol-2-yl, 4H-[1,2,4]-triazol-3-yl, 1,3,4-triazol-2-yl, 1,2,3-triazol-1-yl, 1,2,4-triazol-1-yl, pyridin-2-yl, pyridin-3-yl, pyridin-4-yl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl. Bicyclic throughout aromatic heteroaryl is 9- or 10-membered and contains 1, 2, 3 or 4 heteroatoms selected from O, S or N. Examples are quinolinyl, isoquinolinyl, indolyl, isoindolyl, indolizinyl, benzofuranyl, isobenzofuranyl, benzothiophenyl, benzoxazolyl, benzisoxazolyl, benzthiazolyl, benzoxadiazolyl, benzothiadiazolyl, benzoxazinyl, benzopyrazolyl, benzimidazolyl, benzotriazolyl, benzotriazinyl.

The substituents and indices in the compound of formula (I) are preferably each defined as follows:

Each $R^1$ and $R^{1'}$ is preferably selected from the group consisting of linear $C_1$-$C_{24}$-alkyl, branched $C_3$-$C_{24}$-alkyl, $C_5$-$C_8$-cycloalkyl, $C_6$-$C_{10}$-aryl and $C_6$-$C_{10}$-aryl-$C_1$-$C_{10}$-alkylene, where the rings of cycloalkyl, aryl and aryl-alkylene in the three last-mentioned radicals are unsubstituted or substituted by 1, 2, 3, 4 or 5 identical or different radicals $R^7$.

More preferably, $R^1$ and $R^{1'}$, independently of each other, are selected from the group consisting of linear $C_1$-$C_{24}$-alkyl, branched $C_3$-$C_{24}$-alkyl, $C_5$-$C_8$-cycloalkyl, phenyl and phenyl-$C_1$-$C_{10}$-alkylene, where the rings of cycloalkyl, phenyl and phenyl-alkylene in the three last-mentioned radicals are unsubstituted or substituted by 1, 2 or 3 identical or different substituents $R^7$, wherein $R^7$ is as defined above.

Even more preferably, $R^1$ and $R^{1'}$, independently of each other, are selected from the group consisting of $C_5$-$C_8$-cycloalkyl that is unsubstituted or substituted by one, two or three $C_1$-$C_6$-alkyl substituents; linear $C_4$-$C_{20}$-alkyl; a radical of formula (A.1); a radical of formula (A.2); a radical of formula (A.3); a radical of formula (B.1); or a radical of formula (B.2)

(A.1)

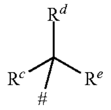

(A.2)

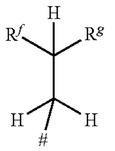

(A.3)

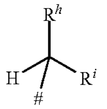

(B. 1)

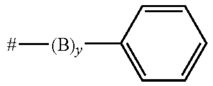

(B. 2)

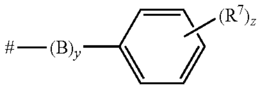

in which # represents the bonding site to the imide nitrogen atom;

$R^c$, $R^d$ and $R^e$, in formula (A.1) are independently selected from $C_1$-$C_{17}$-alkyl, where the sum of the carbon atoms of the $R^c$, $R^d$ and $R^e$ radicals is an integer from 3 to 19;

$R^f$ and $R^g$, in formula (A.2) are independently selected from $C_1$-$C_{17}$-alkyl, where the sum of the carbon atoms of the $R^f$ and $R^g$ radicals is an integer from 2 to 18;

$R^h$ and $R^i$, in formula (A.3), independently from each other are selected from $C_1$-$C_{18}$-alkyl, where the sum of the carbon atoms of the $R^h$ and $R^i$ radicals is an integer from 3 to 19;

B, where present in formulae (B.1) and (B.2), is a $C_1$-$C_{10}$-alkylene group;

y is 0 or 1;

$R^7$ is independently of one another selected from $C_1$-$C_{24}$-alkyl, $C_1$-$C_{24}$-fluoroalkyl, $C_1$-$C_{24}$-alkoxy, fluorine, chlorine or bromine;

z in formula (B.2) is 1, 2 or 3.

Among the radicals of formulae (A.1), (A.2) and (A.3), the radical of formula (A.3) is preferred. In the context of the radical (A.3), $R^h$ and $R^i$ independently of each other, are preferably selected from linear $C_2$-$C_{10}$-alkyl.

Among the radicals of formulae (B.1) and (B.2), those are preferred, in which y is 0, i.e. the variable B is absent. Irrespectively of its occurrence, $R^7$ is preferably selected from $C_1$-$C_{24}$-alkyl, more preferably linear $C_1$-$C_{10}$-alkyl or branched $C_3$-$C_{10}$-alkyl, especially isopropyl or tert-butyl. In particular, the radical of formula (B.2) is preferred. Specific examples of radicals of formula (B.2) are 2,6-dimethylphenyl, 2,4-di(tert-butyl)phenyl, 2,6-diisopropylphenyl or 2,6-di(tert-butyl)phenyl. Most preferably, $R^1$ and $R^{1'}$ have the same meaning and are a radical of formula (B.2), wherein $(B)_y$ is absent.

The term "$C_6$-$C_{10}$-aryloxy" as used with respect to $R^3$, $R^4$, $R^5$ and $R^6$ denotes phenoxy and naphthyloxy.

The term "$C_6$-$C_{10}$-aryl" as used with respect to $R^3$, $R^4$, $R^5$ and $R^6$ denotes phenyl or naphthyl.

The term "$C_2$-$C_{10}$-heteroaryl" as used with respect to $R^3$, $R^4$, $R^5$ and $R^6$ refers to heteroaromatic, monocyclic or bicyclic condensed system with 5, 6, 7, 8, 9, 10, 11, or 12 ring members in which at least one of the rings is aromatic and which contains 1, 2, 3 or 4 heteroatoms selected from N, S or O. Monocyclic heteroaryl groups are preferably 5- or 6-membered hetaryl groups comprising 1, 2 or 3 heteroatoms selected from O, S or N such as 2-furyl (furan-2-yl), 3-furyl (furan-3-yl), 2-thienyl (thiophen-2-yl), 3-thienyl (thiophen-3-yl), 1H-pyrrol-2-yl, 1H-pyrrol-3-yl, pyrrol-1-yl, imidazol-2-yl, imidazol-1-yl, imidazol-4-yl, pyrazol-1-yl, pyrazol-3-yl, pyrazol-4-yl, pyrazol-5-yl, 3-isoxazolyl, 4-isoxazolyl, 5-isoxazolyl, 3-isothiazolyl, 4-isothiazolyl, 5-isothiazolyl, 2-oxazolyl, 4-oxazolyl, 5-oxazolyl, 2-thiazolyl, 4-thiazolyl, 5-thiazolyl, 1,2,4-oxadiazol-3-yl, 1,2,4-oxadiazol-5-yl, 1,3,4-oxadiazol-2-yl, 1,2,4-thiadiazol-3-yl, 1,2,4-thiadiazol-5-yl, 1,3,4-thiadiazol-2-yl, 4H-[1,2,4]-triazol-3-yl, 1,3,4-triazol-2-yl, 1,2,3-triazol-1-yl, 1,2,4-triazol-1-yl, pyridin-2-yl, pyridin-3-yl, pyridin-4-yl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl. Bicyclic throughout aromatic heteroaryl is 9- or 10-membered and contains 1, 2, 3 or 4 heteroatoms selected from O, S or N. Examples are quinolinyl, isoquinolinyl, indolyl, isoindolyl, indolizinyl, benzofuranyl, isobenzofuranyl, benzothiophenyl, benzoxazolyl, benzisoxazolyl, benzthiazolyl, benzoxadiazolyl, benzothiadiazolyl, benzoxazinyl, benzopyrazolyl, benzimidazolyl, benzotriazolyl and benzotriazinyl.

$C_6$-$C_{10}$-aryloxy, $C_2$-$C_{10}$-heteroaryl or $C_6$-$C_{10}$-aryl, are unsubstituted or substituted by one or more identical or different substituents $R^7$.

Preferably, $R^3$, $R^4$, $R^5$ and $R^6$, independently of each other, are selected from phenoxy and phenoxy, which is substituted by one, two, or three substituents $R^7$, especially $C_1$-$C_{12}$-alkyl substituents wherein in case of two, or three $C_1$-$C_{12}$-alkyl substituents, the $C_1$-$C_{12}$-alkyl substituents may be the same or different, but are preferably the same. More preferably, $R^3$, $R^4$, $R^5$ and $R^6$ are each phenoxy which is substituted by a $C_1$-$C_{12}$-alkyl substituent in the para-position position and optionally in one ortho-position or both ortho-positions by $C_1$-$C_{12}$-alkyl substituents.

Likewise preferably, $R^3$, $R^4$, $R^5$ and $R^6$, independently of each other, are selected from thienyl, pyridinyl, quinolinyl and isoquinolinyl, which are optionally substituted by one, or more substituents $R^7$, especially $C_1$-$C_{12}$-alkyl substituents.

Likewise preferably, $R^3$, $R^4$, $R^5$ and $R^6$, independently of each other, are selected from 1-naphthyl and 2-naphthyl, which are unsubstituted or substituted by one, two or three substituents $R^7$, especially $C_1$-$C_{12}$-alkyl substituents.

In a particularly preferred embodiment, $R^3$, $R^4$, $R^5$ and $R^6$, independently of each other, are selected from phenyl and phenyl, which is substituted by one, two, or three substituents $R^7$, especially $C_1$-$C_{12}$-alkyl substituents wherein in case of two, or three $C_1$-$C_{12}$-alkyl substituents, the $C_1$-$C_{12}$-alkyl substituents may be the same or different, but are preferably the same. More preferably, $R^3$, $R^4$, $R^5$ and $R^6$ are each phenyl which is substituted by a $C_1$-$C_{12}$-alkyl substituent in the para-position position and optionally in one ortho-position or both ortho-positions by $C_1$-$C_{12}$-alkyl substituents. Specific examples are phenyl, 2,4-di(tert-butyl)phenyl, 4-isopropylphenyl, 2,4-diisopropylphenyl, 4-(tert-butyl) phenyl, 4-(tert-octyl)phenyl and 2,4-di(tert-butyl)phenyl.

Preferably, $R^7$ is $C_1$-$C_{15}$-alkyl, especially linear $C_1$-$C_{12}$-alkyl or branched $C_1$-$C_{12}$-alkyl. Examples for linear $C_1$-$C_{12}$-alkyl are methyl, ethyl, n-propyl, n-butyl, n-hexyl, n-heptyl, n-octyl, n-nonyl, n-decyl, n-undecyl or n-dodecyl. Examples for branched $C_1$-$C_{12}$-alkyl are sec-butyl, isobutyl, tert-butyl, 2-methylpropyl (isopropyl), 1,1-dimethylethyl (tert-butyl), pentyl, 1-methylbutyl, 2-methylbutyl, 3-methylbutyl, 2,2-dimethylpropyl, 1-ethylpropyl, 1,1-dimethylbutyl, 2,2-dimethyl-butyl, 1-methylpentyl, 2-methylpentyl, 1-methylhexyl, 1-ethylpentyl, 1-methylheptyl, 2-ethylhexyl, 6-methylheptyl (isooctyl), 1,1,3,3-teramethylbutyl (tert-octyl), isononyl, 1,1-dimethylheptyl, isodecyl and the isopropyl and the position isomers thereof.

Preferably, $R^8$ is $C_1$-$C_{15}$-alkyl, especially linear $C_1$-$C_{12}$-alkyl or branched $C_1$-$C_{12}$-alkyl. Examples for linear $C_1$-$C_{12}$-alkyl are methyl, ethyl, n-propyl, n-butyl, n-hexyl, n-heptyl, n-octyl, n-nonyl, n-decyl, n-undecyl or n-dodecyl. Examples for branched $C_1$-$C_{12}$-alkyl are sec-butyl, isobutyl, tert-butyl, 2-methylpropyl (isopropyl), 1,1-dimethylethyl (tert-butyl), pentyl, 1-methylbutyl, 2-methylbutyl, 3-methylbutyl, 2,2-dimethylpropyl, 1-ethylpropyl, 1,1-dimethylbutyl, 2,2-dimethyl-butyl, 1-methylpentyl, 2-methylpentyl, 1-methylhexyl, 1-ethylpentyl, 1-methylheptyl, 2-ethylhexyl, 6-methylheptyl (isooctyl), 1,1,3,3-teramethylbutyl (tert-octyl), isononyl, 1,1-dimethylheptyl, isodecyl and the isopropyl and the position isomers thereof.

Even more preferably, the substituents and indices in the compounds of formula (I) are each defined as follows:

n is 0 or 1, especially 0;

$R^1$ and $R^{1'}$ are identical and are selected from $C_4$-$C_{20}$-alkyl, $C_5$-$C_8$-cycloalkyl or phenyl, wherein the two last-mentioned substituents may be substituted by one, two or three $C_1$-$C_{12}$-alkyl substituents;

$R^3$, $R^4$, $R^5$ and $R^6$, independently of each other are, phenoxy; especially phenoxy, which is substituted by one substituent $R^7$, and optionally by one or two $C_1$-$C_{12}$-alkyl substituents;

very especially phenoxy is substituted by $R^7$ in the para-position and optionally by one or two $C_1$-$C_{12}$-alkyl substituents; more specifically, phenoxy is substituted by $R^7$ in the para-position and optionally in one ortho-position or both ortho-positions by $C_1$-$C_{12}$-alkyl substituents; or $R^3$, $R^4$, $R^5$ and $R^6$, independently of each other are, thienyl, pyridinyl, quinolinyl and isoquinolinyl, which are optionally substituted by one, two or three substituents $R^7$; $R^3$, $R^4$, $R^5$ and $R^6$, independently of each other are, 1-naphthyl and 2-naphthyl, which are optionally substituted by one, two or three substituents $R^7$;

$R^3$, $R^4$, $R^5$ and $R^6$, independently of each other are, phenyl, especially phenyl, which is substituted by one substituent $R^7$, and optionally by one or two $C_1$-$C_{12}$-alkyl substituents; very especially, phenyl which is substituted by $R^7$ in the para-position and optionally by one or two $C_1$-$C_{12}$-alkyl substituents; more specifically, phenyl is substituted by $R^7$ in the para-position and optionally in one ortho-position or both ortho-positions by $C_1$-$C_{12}$-alkyl substituents;

$R^7$ is $C_1$-$C_{12}$-alkyl.

Preferred compounds of the formula (I) are especially those of the formula (Ia)

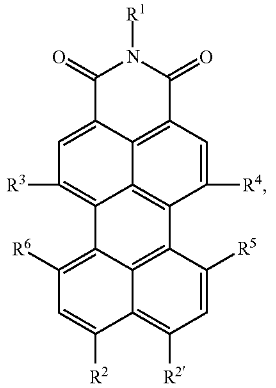

wherein $R^1$ is selected from $C_4$-$C_{20}$-alkyl, $C_5$-$C_8$-cycloalkyl or phenyl, wherein the two last-mentioned substituents are substituted by one, two or three $C_1$-$C_6$-alkyl substituents;

$R^3$, $R^4$, $R^5$ and $R^6$ have the same meaning and are selected from phenyl, phenoxy; especially phenoxy, which is substituted by one, two or three substituents $R^7$, wherein $R^7$ is preferably $C_1$-$C_{12}$-alkyl; thienyl, pyridinyl, quinolinyl, isoquinolinyl; 1-naphthyl, 2-naphthyl, which are substituted by one, two or three substituents $R^7$, and phenyl, which is substituted by one, two or three substituents $R^7$, wherein $R^7$ is preferably $C_1$-$C_{12}$-alkyl, very especially phenyl which is substituted by $R^7$ in the para-position; and $R^2$ and $R^{2'}$ together form a group of the formula

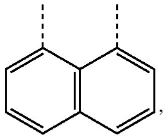, 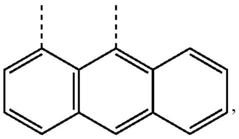,

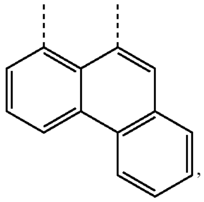, 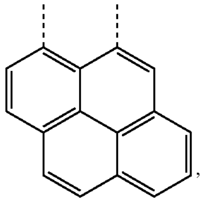,

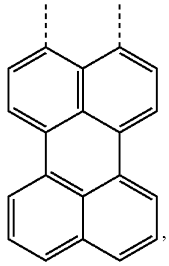, 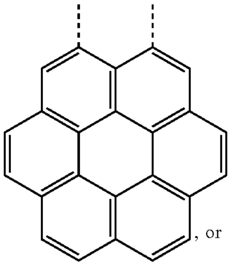, or

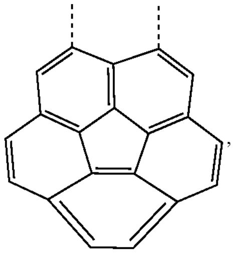, wherein represents the bond to the rylene basic skeleton.

$R^7$ has one of the above general or, in particular, one of the above preferred meanings.

Preferred compounds of the formula (I) are also those of the formula (Ib)

(Ib)

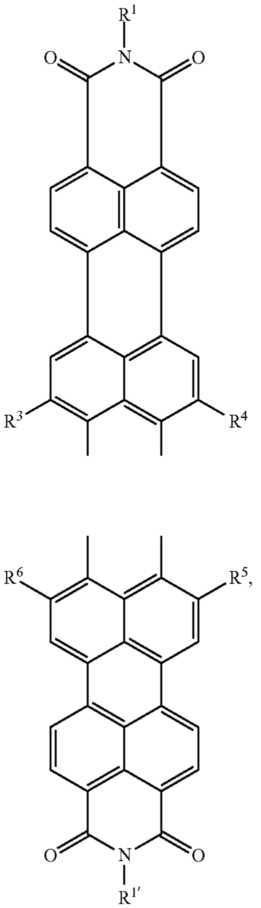

wherein $R^1$ and $R^{1'}$ have the same meaning and are selected from $C_4$-$C_{20}$-alkyl, $C_5$-$C_8$-cycloalkyl or phenyl, wherein the two last-mentioned substituents are substituted by one, two or three $C_1$-$C_6$ alkyl substituents;

$R^3$, $R^4$, $R^5$ and $R^6$ have the same meaning and are selected from phenyl, phenoxy; especially phenoxy, which is substituted by one, two or three substituents $R^7$, wherein $R^7$ is preferably $C_1$-$C_{12}$-alkyl; thienyl, pyridinyl, quinolinyl, isoquinolinyl; 1-naphthyl, 2-naphthyl, which are substituted by one, two or three substituents $R^7$, and phenyl, which is substituted by one, two or three substituents $R^7$, wherein $R^7$ is preferably $C_1$-$C_{12}$-alkyl, very especially phenyl which is substituted by $R^7$ in the para-position.

$R^7$ has one of the above general or, in particular, one of the above preferred meanings.

Most preferred $R^3$, $R^4$, $R^5$ and $R^6$ have the same meaning and are selected from phenyl, which is substituted by one, two or three substituents $R^7$, wherein $R^7$ is preferably $C_1$-$C_{12}$-alkyl, very especially phenyl is substituted by $R^7$ in the para-position.

Examples of preferred compounds are shown below:
(7')
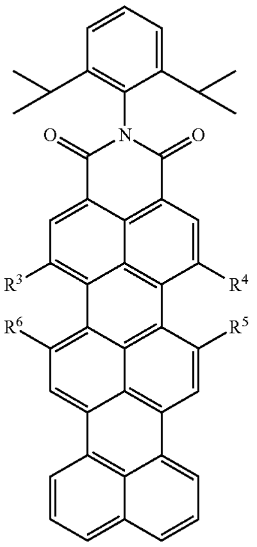
| Compound | $R^3 = R^4 = R^5 = R^6$ |
| --- | --- |
| 7a | 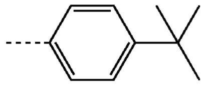 |
| 7c | 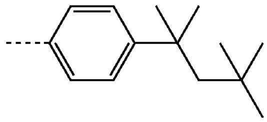 |
(7'')
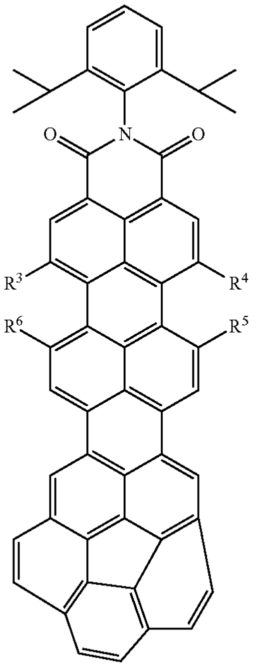
| Compound | $R^3 = R^4 = R^5 = R^6$ |
| --- | --- |

-continued

| | |
|---|---|
| 7b | 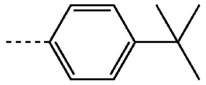 |
| 7d | 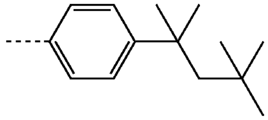 |

(10)

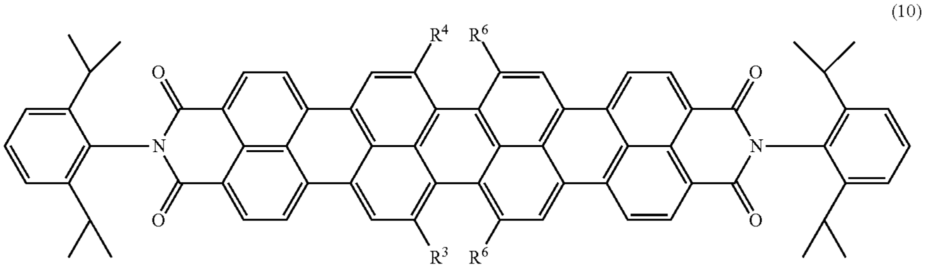

| Compound | $R^3 = R^4 = R^5 = R^6$ |
|---|---|
| 10a | 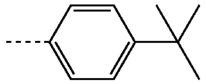 |
| 10b | 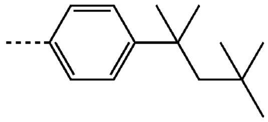 |

A further aspect of the present invention is a process for the preparation of a compound of formula (I)

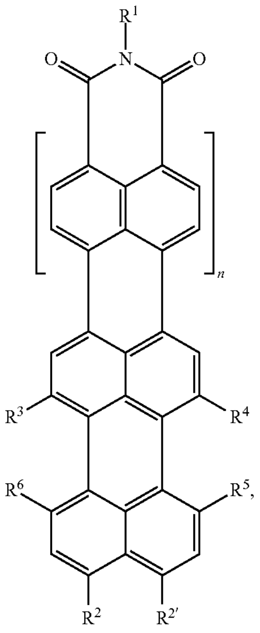

comprising i) reacting a compound of formula (VI)

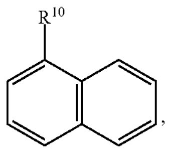

the compound of formula (VI) is unsubstituted or substituted with one or more substituents $R^7$, or the compound of formula (VI) may be part of an annulated ring system, which is unsubstituted or substituted with one or more substituents $R^7$; with a compound of formula (V)

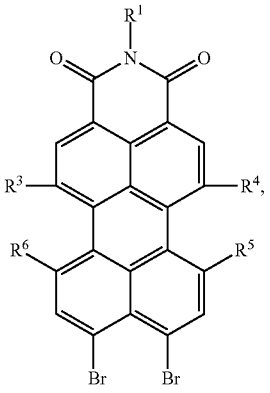

in a solvent and in the presence of a catalyst, or comprising i) reacting a compound of formula (VI')

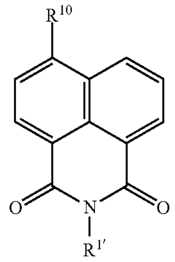

the compound of formula (VI') is unsubstituted or substituted with one or more substituents $R^7$; with a compound of formula (IV)

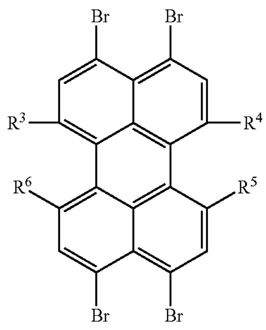

in a solvent and in the presence of a catalyst, wherein $R^{10}$ is $-B(OH)_2$, $-B(OY^1)_2$,

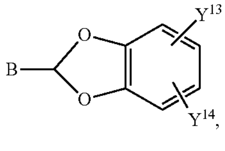

or

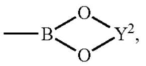

wherein $Y^1$ is independently in each occurrence a $C_1$-$C_{10}$alkyl group and $Y^2$ is independently in each occurrence a $C_2$-$C_{10}$alkylene group and $Y^{13}$ and $Y^{14}$ are independently of each other hydrogen, or a $C_1$-$C_{10}$alkyl group; and n; $R^a$; $R^1$, $R^{1'}$; $R^3$, $R^4$, $R^6$; $R^6$; $R^2$ and $R^{2'}$ are defined above.

The compounds of formula (IV)

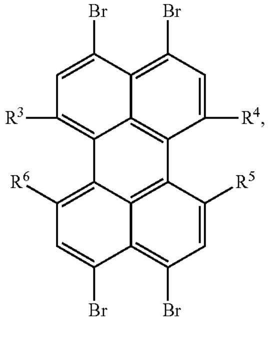

or

-continued (V)

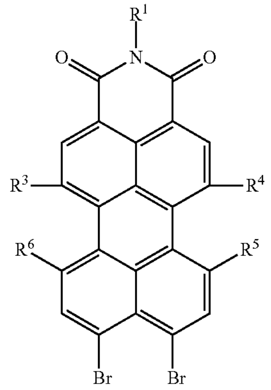

represents intermediates in the preparation of the compounds of formula (I) and form a further aspect of the present invention. $R^1$, $R^3$, $R^4$, $R^5$ and $R^6$ are defined above, or below.

Preferably, $R^3$, $R^4$, $R^5$ and $R^6$, independently of each other, are selected from thienyl, pyridinyl, quinolinyl and isoquinolinyl, which are optionally substituted by one, or more substituents $R^7$, especially $C_1$-$C_{12}$-alkyl substituents, especially thienyl, pyridinyl, quinolinyl and isoquinolinyl; 1-naphthyl and 2-naphthyl, which are unsubstituted or substituted by one, two or three substituents $R^7$, especially $C_1$-$C_{12}$-alkyl substituents; very especially phenyl, which is substituted by one, two, or three substituents $R^7$, especially $C_1$-$C_{12}$-alkyl substituents wherein in case of two, or three $C_1$-$C_{12}$-alkyl substituents, the $C_1$-$C_{12}$-alkyl substituents may be the same or different, but are preferably the same.

Most preferred, $R^3$, $R^4$, $R^5$ and $R^6$ have the same meaning and are selected from phenyl, which is substituted by one, two or three substituents $R^7$, wherein $R^7$ is preferably $C_1$-$C_{12}$-alkyl, specifically, phenyl is substituted by $R^7$ in the para-position. Specific examples are phenyl, 2,4-di(tert-butyl)phenyl, 4-isopropylphenyl, 2,4-diisopropylphenyl, 4-(tert-butyl)phenyl, 4-(tert-octyl)phenyl and 2,4-di(tert-butyl)phenyl.

Preference is given to effecting the reaction in the presence of catalytically active amounts of a transition metal of transition group VIII of the Periodic Table (group 10 according to IUPAC), for example nickel, palladium or platinum, especially in the presence of a palladium catalyst. Suitable catalysts are, for example, selected palladium-phosphine complexes, such as, for example, $Pd(PPh_3)_2Cl_2$, $Pd(PPh_3)_4$, $Pd(dba)_2$, $Pd_2(dba)_3$, $PdCl_2$, Palladium(II) acetate ($Pd(OAc)_2$), $[Pd(allyl)Cl]_2$, $Pd(dppf)Cl_2$, $PdBr_2(PtBu_3)_2$, $Pd(crotyl)(PtBu_3)Cl$, $Pd(PtBu_3)_2$, $Pd(Amphos)_2Cl_2$, Pd(allyl)(Amphos)Cl, $Pd(Binap)Br_2$, $Pd(dcpp)Cl_2$, $Pd(DiPrPF)Cl_2$, Pd-PEPPSI-IPr, Chloro(2-dicyclohexylphosphino-2',4',6'-triisopropyl-1,1'-biphenyl)[2-(2-aminoethyl)phenyl)]palladium(II) (also known as XPhos Precatalyst 1st Generation), Chloro-(2-dicyclohexylphosphino-2',4',6'-triisopropyl-1,1-biphenyl)[2-(2'-amino-1,1-biphenyl)] palladium(II) (also known as XPhos Precatalyst 2nd Generation), Chloro(2-dicyclohexylphosphino-2',6'-dimethoxy-1,1-biphenyl)[2-(2-aminoethylphenyl)]palladium(II) (also known as SPhos Precatalyst 1st Generation), Chloro(2-dicyclohexylphosphino-2',6'-dimethoxy-1,1'-biphenyl)[2-(2'-amino-1,1'-biphenyl)] palladium(II) (also known as XPhos Precatalyst 2nd Generation), Chloro(2-dicyclohexylphosphino-2',6'-diisopropoxy-1,1-biphenyl)[2-(2-aminoethylphenyl)]palladium (II) (also known as RuPhos Precatalyst 1st Generation), Chloro(2-dicyclohexylphosphino-2',6'-diisopropoxy-1,1'-biphenyl)[2-(2'-amino-1,1-biphenyl)]palladium(II) (also known as RuPhos Precatalyst 2nd Generation), Pd, palladium on activated carbon in the presence of phosphine compounds, and palladium(II) compounds such as palladium(II) chloride or bis(acetonitrile)palladium(II) chloride in the presence of phosphine ligands.

The ligand may be one or more ligands selected from the group of $PPh_3$, $P(oTol)_3$, $P(oTol)Ph_2$, $P(pTol)_3$, $PtBu_3$, $PtBu_3$*$HBF_4$, $PCy_3$, PCy3*$HBF_4$, $P(OiPr)_3$, DPE-Phos, dppf, dppe, dppp, dcpp, dppb, $P(Furyl)_3$, CPhos, SPhos, RuPhos, XPhos, DavePhos, JohnPhos and Xantphos. The ligand may be present in a range from about 2 mol % to about 50 mol %.

Especially suitable organometallic compounds (VI) are an appropriately substituted arylboronic acid and arylboronic esters of formula (VI), where $R^{10}$=$B(OH)_2$ or —$B(OY^1)_2$ where $Y^1$=$C_1$-$C_4$-alkyl, or

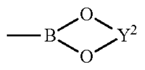

where $Y^1$=$C_2$-$C_4$-alkylene optionally bearing 1, 2, 3 or 4 substituents selected from $C_1$-$C_4$-alkyl.

The arylboronic acids and esters thereof are known from the literature, commercially available, or can be prepared from the corresponding arylmagnesium compounds by reaction with appropriate boric esters.

The reaction of (IV) with the organometallic compound (VI), especially in the case of the Suzuki coupling, is effected under basic conditions. Suitable bases are alkali metal carbonates and alkali metal hydrogencarbonates such as sodium carbonate, potassium carbonate, cesium carbonate, sodium hydrogencarbonate, alkaline earth metal carbonates and alkaline earth metal hydrogencarbonates such as magnesium carbonate or magnesium hydrogencarbonate, or tertiary amines such as triethylamine, trimethylamine, triisopropylamine or N-ethyl-N-diisopropylamine.

Typically, the coupling of the compound of formula (IV) with the compound of formula (VI) is effected in a solvent. Suitable solvents are organic solvents such as aromatics, e.g. toluene, mesitylene, 1-chloronaphthalene, acyclic ethers, e.g. 1,2-dimethoxyethane, cyclic ethers such as tetrahydrofuran or 1,4-dioxane, polyalkylene glycols such as diethylene glycol, carbonitriles such as acetonitrile, propionitrile, carboxamides such as dimethylformamide or dimethylacetamide, or mixtures thereof. In the Suzuki coupling, the aforementioned solvents can also be used in a mixture with water; for example, the ratio of organic solvent to water may be in the range from 5:1 to 1:5.

The reaction temperature is generally within the range of 30 to 180° C.

At least one mole of the organometallic compound (VI) is used per mole of halogen atom to be exchanged. It may be advantageous to use a 5 to 30% molar excess of organometallic compound of the formula (VI) per mole of halogen atom to be exchanged. Compounds of the formula (VI) can be prepared according to known methods in the art.

All reactions are typically carried out in the absence of oxygen and moisture. As a rule, the reaction mixtures are worked up in the customary manner, for example by mixing with water, separating the phases, and, if appropriate purifying the crude product by chromatography. If the end product is obtained as solids, they may be purified by recrystallization.

The compounds of the present invention can be prepared by using routine techniques familiar to a skilled person. In particular, the compounds of the formula (I) can be prepared according to the following routes or as described in the experimental part of this application.

A developed reaction sequence gives synthetic access to new π-extended, aryl-substituted rylene dicarboximide dyes. Starting from literature-known compound 1 (M. Queste, C. Cadiou, B. Pagoaga, L. Giraudet, N. Hoffmann, New J. Chem. 2010, 34, 2537-2545 [15]) and applying literature-known reaction conditions for fourfold Suzuki-Miyaura cross coupling with para-tert-butylphenyl boronic acid tetraaryl-substituted 2 could be synthesized in 67% yield.

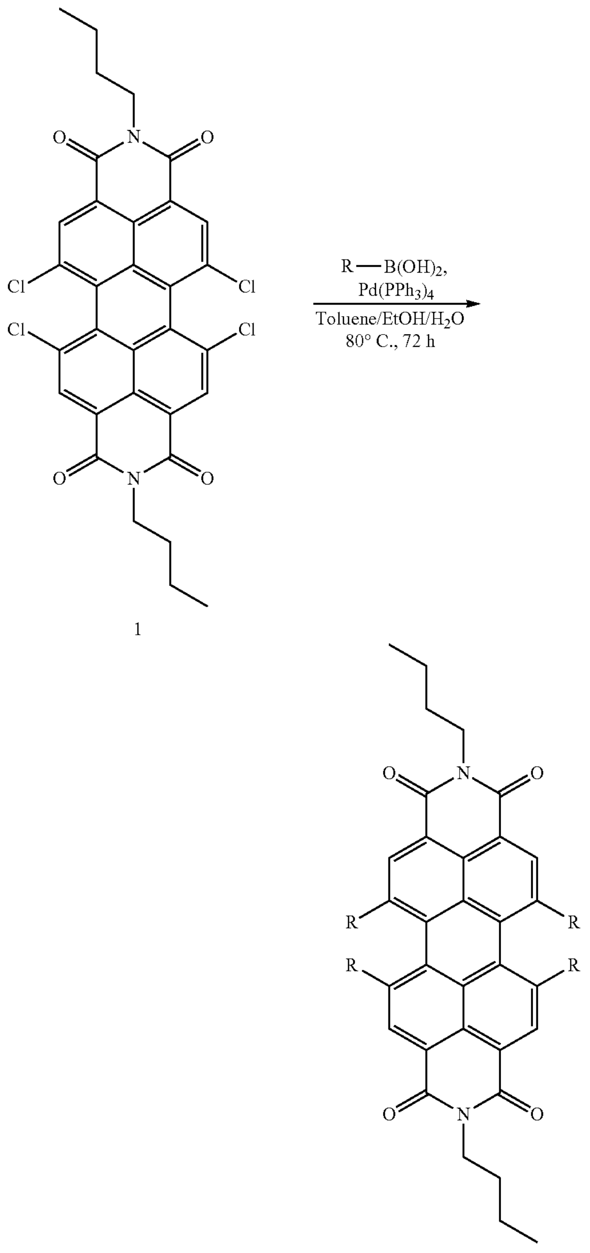

1

2

Under typically saponification reaction conditions with potassium hydroxide, 2 could be converted into 3 in 77% yield. Subsequently, Hunsdiecker-like reaction conditions give the partial decarboxylated and double-brominated species 4a and the fully decarboxylated and fourfold-brominated compound 4b in yields of 25% and 37%, respectively.

2

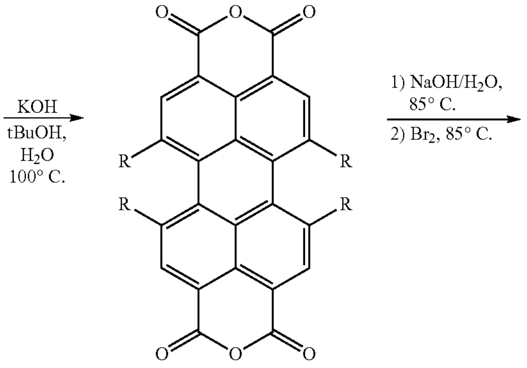

3

-continued

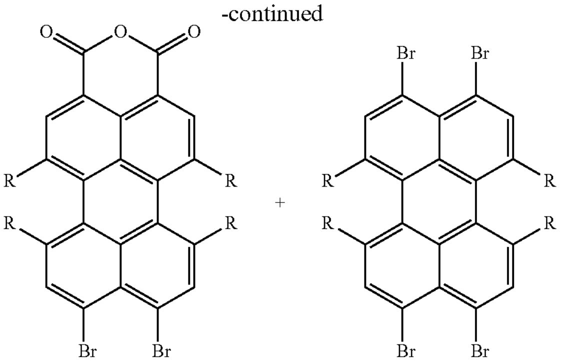

4a

4b

An imidization reaction of 4a with 2,6-diisopropylaniline give 5 in a yield of 48%. The dicarboximide 5 could then be reacted with 6a or 6b in a palladium-catalyzed annulation reaction. The respective products 7a and 7b could be isolated in yields of 19% (7a) and 15% (7b).

4a

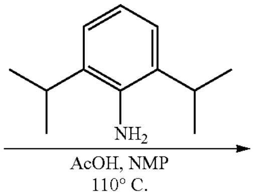

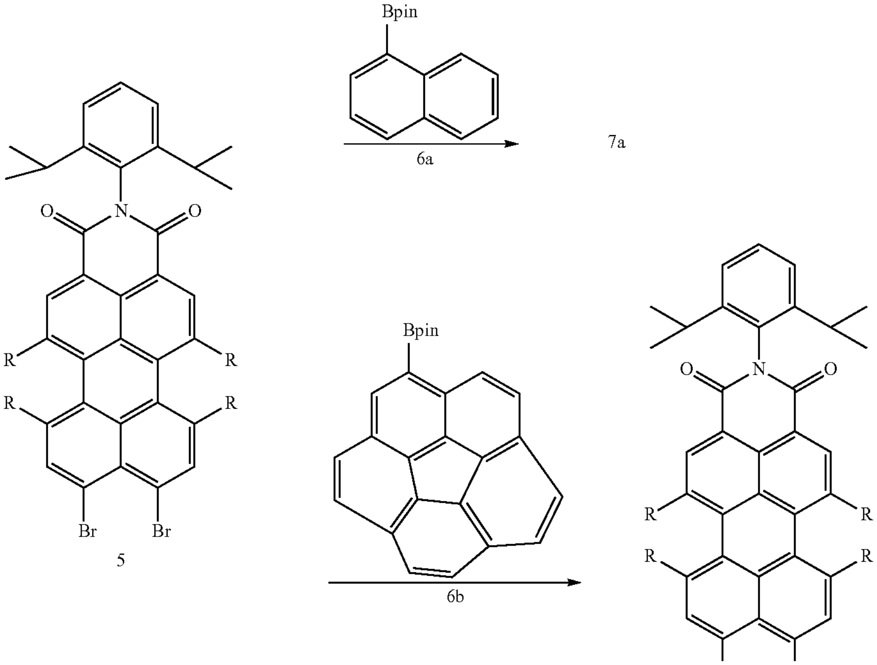

5

6a

7a

6b

-continued

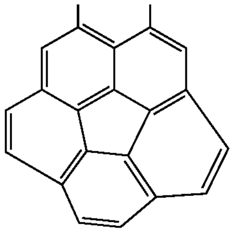

7b

Furthermore, compound 7a was also accessible by fourfold Suzuki-Miyaura cross coupling of 8a with para-tert-butylphenyl boronic acid (6%).

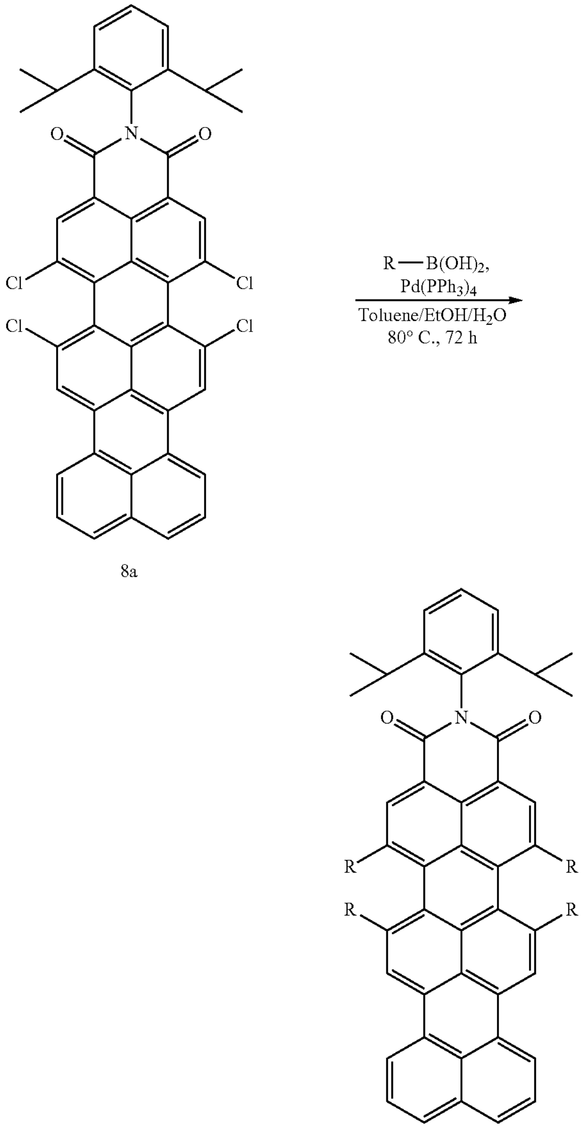

8a

7a

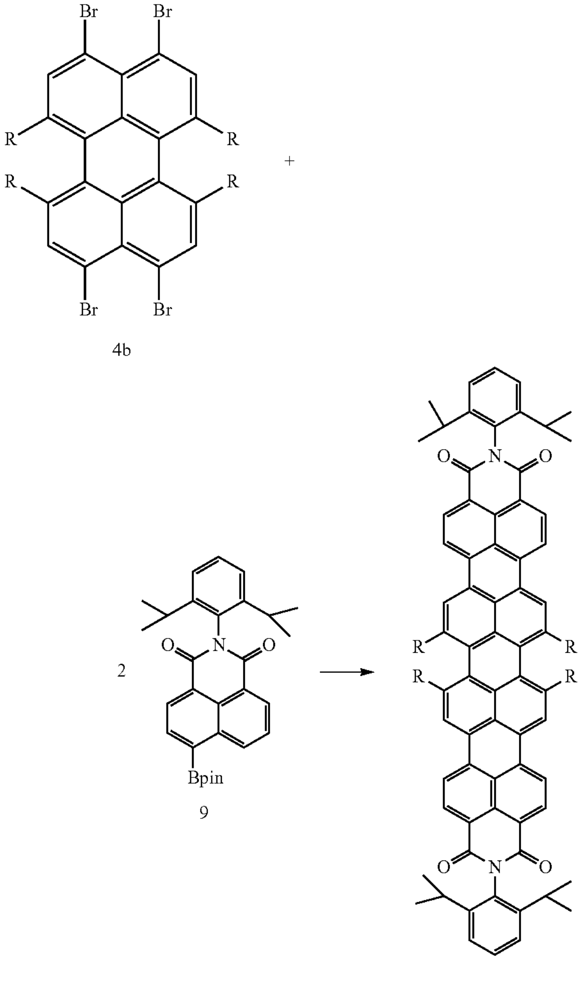

4b

+

2

9

10a

R =

Bpin =

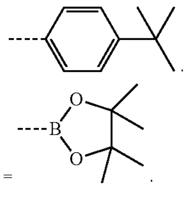

The fourfold brominated compound 4b was used in a twofold annulation reaction with 9 and the desired product 10a was isolated in a yield of 15%.

Figure 2:
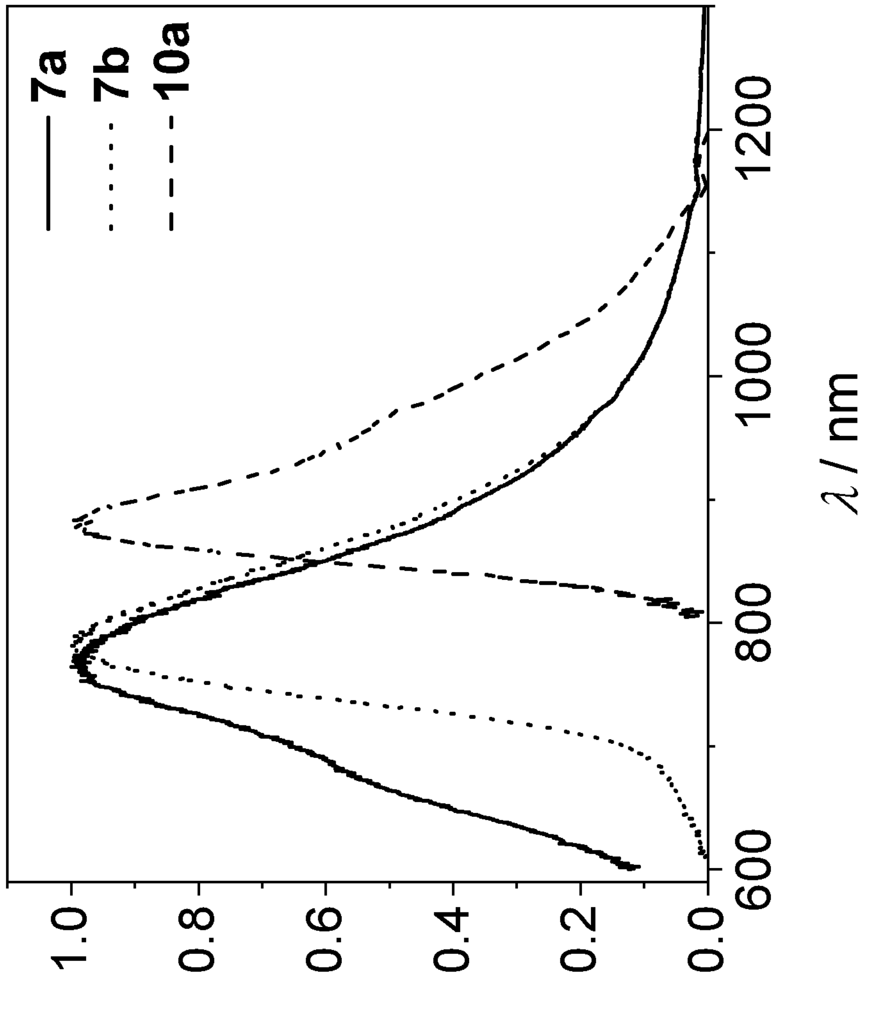
FIG. 2: Fluorescence spectra of 7a (λex=590 nm), 7b (λex=600 nm) and 10 (λex=790 nm) in dichloromethane solutions at room temperature.

The optical properties of 7a, 7b and 10a were investigated with UV/vis/NIR absorption and fluorescence spectroscopy in dichloromethane solutions at room temperature (FIG. 1, FIG. 2 and Table 1).

TABLE 1

Summary of the optical properties of 7a ($\lambda_{ex}$ = 590 nm), 7b ($\lambda_{ex}$ = 600 nm) and 10a ($\lambda_{ex}$ = 790 nm) measured in $CH_2Cl_2$ (c ≈ 1 × $10^{-5}$M − 1 − $10^{-6}$M) at room temperature.

| | $\lambda_{abs}$/nm ($\varepsilon$/$M^{-1}cm^{-1}$) | $\lambda_{em}$/nm | Stokes Shift/ $cm^{-1}$ | $\Phi_{fl}$/%[a] | τ/ns |
|---|---|---|---|---|---|
| 7a | 679 (19800) | 768 | 1700 | 1.4 ± 0.1 | 0.43 ± 0.022 (18.2%)<br>2.59 ± 0.075 (44.9%)<br>7.03 ± 0.133 (36.9%) |
| 7b | 682 (14300) | 786 | 1940 | 4.8 ± 0.1 | 0.62 ± 0.002 (90.2%)<br>5.38 ± 0.06 (9.8%) |
| 10a | 811 (67000) | 884 | 1020 | 1.3 ± 0.1 | 0.22 ± 0.006 (66.3%)<br>0.98 ± 0.031 (30.2%)<br>4.21 ± 0.365 (3.5%) |

[a]Fluorescence quantum yields were determined using the relative method and Oxazine1 or IR125 as reference.

The substitution of the chlorine atoms with aryl groups in 7a causes the bathochromic shift in the UV/vis/NIR spectrum (8a: λabs=623 nm (48500 $M^{-1}cm^{-1}$); 7a: λabs=679 nm (19800 $M^{-1}cm^{-1}$)). The bathochromic shift is also present in the comparison of the aryl-substituted compound 7b (7b: λabs=682 nm (14300 $M^{-1}cm^{-1}$)) and its chlorinated counterpart (λabs=614 nm (50400 $M^{-1}cm^{-1}$))(M. Mahl, K. Shoyama, J. Rühe, V. Grande, F. Würthner, Chem. Eur. J. 2018, 24, 9409-9416 [13]). The redshift due to the respective substituent is similar to the one observed for literature-known tetrachloro-PBI [1] and tetraaryl-PBI ([14, [15], [16]).

The absorption maximum of the quaterrylene bisimide 10a has with 811 nm an even more pronounced redshift and the extinction coefficient is high (67000 $M^{-1}$ cm-1). This large bathochromic shift is attributed to the longitudinal expanded π-scaffold and the second electron-withdrawing dicarboximide unit ([3]).

With the introduction of aryl groups the emission maxima with 768 nm for 7a and 786 nm for 7b are significantly shifted into the NIR region. Compared to the chlorinated counterparts of 7a and 7b the emission maximum is 10 nm (for 7a) and 77 nm (for 7b) redshifted ([13]). Whilst for 7a only a fluorescence quantum yield of 1.4% is obtained, 7b exhibits a higher fluorescence quantum yield of 4.8%. The fluorescence of the quaterrylene bisimide 10a with an emission maximum of 884 nm is the farthest in the NIR region and for such a small band gap (where non-radiative decay via internal conversion is fast) the quantum yield of 1.4% is quite high (S. K. Lee, Y. Zu, A. Herrmann, Y. Geerts, K. Müllen, A. J. Bard, J. Am. Chem. Soc. 1999, 121, 3513-3520 [17]).

In comparison, the absorption maximum of a pure quaterrylene is located at 659 nm (K. Koch, K. Müllen, Chem. Ber. 1991, 124, 2091-2100 [18]). It has a higher fluorescence quantum yield of 5% but this is not outstanding because the emission maximum is with 678 nm>200 nm blue-shifted compared to 10a. Likewise, the parent quaterrylene bisimides typically show absorption at shorter wavelengths compared to 10a, and only weak or no emission is observed ([7], [8], C. Liu, S. Zhang, J. Li, J. Wei, K. Müllen, M. Yin, Angew. Chem. Int. Ed 2019, 58, 1638-1642 [19]). A piperidyl-substituted quaterrylene bisimide has been reported with an extraordinary redshifted absorption maximum (λabs=910 nm) compared to 10a. But no information about emission properties were given which suggests that this dye does not fluoresce (DE102004057585).

Figure 3:
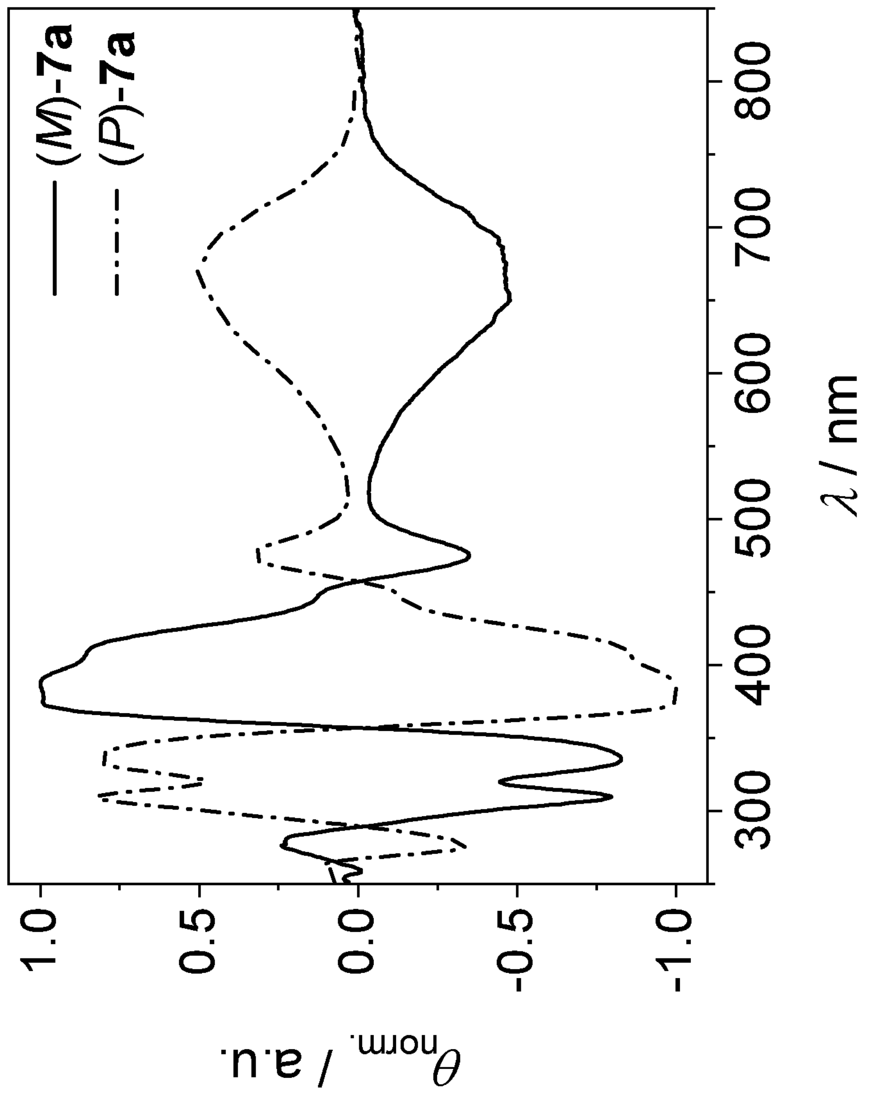
FIG. 3: Normalized CD spectra of both enantiomers, (M)-7a and (P)-7a in n-hexan/dichloromethane-mixture (2/1) at 20° C.

As another benefit, for sterically demanding substituents on the polyaromatic dicarboximide scaffold atropo-enantiomers are formed (FIG. 3). For fourfold bay-substituted PBIs, those with aryl groups have much higher racemization barriers than those with chloro or aryloxy substituents (P. Osswald, F. Würthner, J. Am. Chem. Soc. 2007, 129, 14319-14326 [21]). For compound 7a with its aryl substituents, the two enantiomers could be separated by chiral HPLC using a n-hexane/dichloromethane mixture (2/1) as eluent at room temperature. The chiroptical properties of the separated enantiomers were investigated after separation by circular dichroism (CD) spectroscopy. The first eluted fraction shows a negative signal for the lowest energy transition and can therefore be assigned as (M)-7a. The second fraction shows a mirror image relation and can thus be assigned as (P)-configuration of 7a. Subsequently, the stability against racemization was determined by time-dependent CD spectroscopy. At room temperature as well as at 35° C. no significant change in the CD spectrum was observed over several hours. Therefore, another sample was heated to 85° C. in 1,1,2,2-tetrachloroethane for 60 hours, whereby still no distinct decrease of the CD signal could be detected. This observation is consistent with earlier results that tetraaryl-substituted PBIs have a very high racemization barrier (estimated: 250 kJ/mol at 180 K ([16], [21]).

The combination of NIR absorption and NIR emission with stable chirality even at elevated temperature makes the newly reported dyes outstanding chiroptical molecular probes.

The compounds of the formula (I) according to the invention may be incorporated without any problem into organic and inorganic materials and are therefore suitable for a whole series of end uses, some of which will be listed by way of example below.

In general, the compounds of formula (I) are fluorescent dyes that absorb light having a wavelength in the range from 450 to 950 nm. They generally have their absorption maximum in the range from 600 to 880 nm. They generally emit light in a range from 615 to 950 nm. The fluorescence light thus generated is advantageously detected with a semiconductor detector, especially with a silicon photodiode or a germanium photodiode. For these applications, it is important to use the compound of formula (I) in high concentration to convert as much of the absorbed light as possible.

The compounds of formula (I) are outstandingly suitable for homogeneously coloring high molecular weight organic and inorganic materials, in particular, for example, plastics, in particular thermoplastics, coatings and printing inks, and also oxidic layer systems.

NIR spectroscopy is a well-established technique for detecting both chemical and physical properties of various materials. For example, NIR spectroscopy may be used for a non-destructive food analysis or for a non-destructive plant analysis in agriculture. The compounds of formula (I) are also especially useful as fluorescent dye in a near infrared spectrometer apparatus for providing light having a wavelength in the range from 680 to 950 nm.

The compounds of formula (I) are also of interest as active components in photovoltaics. Thus, the present invention also relates to the use of the compounds of formula (I) in photovoltaic applications, especially in a fluorescent solar concentrator. The solar concentrator is based on solar cells and a polymeric matrix material comprising the compound of formula (I) and the solar cells are located at the outer edges of the polymeric material.

The compounds of formula (I) are also of interest as dye for laser applications.

The compounds of formula (I) are also of interest as semiconductor in organic electronic applications, especially as semiconductor in an organic field effect transistor or as semiconductor in an organic electroluminescent device. The compounds of formula (I) may also be used as semiconductor in dye-sensitized solar cells.

Moreover, the compounds of formula (I) are suitable as near infrared absorbers for heat management and as NIR laser beam-absorbent materials in the fusion treatment of plastics parts. These applications are described in detail, for example, in DE 10 2004 018 547, WO 02/77081 and WO 04/05427.

Moreover, the compounds of formula (I) may also be used advantageously for laser marking and laser inscription. In this case, the laser light absorbed by the compound of formula (I) brings about heating of the plastic, which leads to it foaming or the conversion of a dye present in addition, and in this way gives rise to a marking or inscription.

The compounds of formula (I) are also of interest as labeling groups in detection methods, especially in diagnostic and analytical methods on biological samples, including living cells.

The compounds of formula (I) are also of interest for use in an ink for machine readability and/or security applications.

The compounds of formula (I) owing to their pronounced absorption in the near infrared region of the electromagnetic spectrum, are also of interest for obtaining markings and inscriptions which absorb near infrared light and are invisible to the human eye. Thus, the present invention also relates to the use of the compound of formula (I) as defined above for brand protection or as marker for liquids. Useful liquids which can be marked with the compounds of the formula (I) preferably include oils such as mineral oils, vegetable and animal fatty oils, and ethereal oils.

Examples of such oils are natural oils such as olive oil, soybean oil or sunflower oil, or natural or synthetic motor oils, hydraulic oils or transmission oils, for example motor vehicle oil or sewing machine oil, or brake fluids and mineral oils which, according to the invention, comprise gasoline, kerosene, diesel oil and also heating oil. Particular preference is given to mineral oils such as gasoline, kerosene, diesel oil or heating oil, in particular gasoline, diesel oil or heating oil. Particularly advantageously, the above-mentioned compounds of the formula (I) are used as markers for mineral oils in which labeling is simultaneously required, for example for tax reasons. In order to minimize the costs of labeling, but also in order to minimize possible interactions of the marked mineral oils with any other ingredients present, such as polyisobuteneamine (PIBA), efforts are made to minimize the amount of markers. A further reason to minimize the amount of markers may be to prevent their possible harmful influences, for example on the fuel intake and exhaust gas outlet region of internal combustion engines.

The compounds of the formula (I) to be used as markers are added to the liquids in such amounts that reliable detection is ensured. Typically, the (weight-based) total content of markers in the marked liquid is from about 0.1 to 5000 ppb, preferably from 1 to 2000 ppb and more preferably from 1 to 1000 ppb.

The compounds of the formula (I) may if appropriate also be used in a mixture with other markers/dyes.

To mark the liquids, the compounds are generally added in the form of solutions. Especially in the case of mineral oils, suitable solvents for providing these stock solutions are preferably aromatic hydrocarbons such as toluene, xylene or relatively high-boiling aromatics mixtures.

The compounds of formula (I) can also be used in the form of a mixture, comprising the compound of formula (I) and at least one further IR absorber different from the compound of formula (I). Suitable further IR absorbers are in principle all known classes of IR absorbers that are compatible with the compound of formula (I). Preferred further IR absorbers are selected from polymethines, phthalocyanines, naphthalocyanines, quinone-diimmonium salts, aminium salts, rylenes, inorganic IR absorbers and mixtures thereof. Further polymethine IR absorbers are preferably selected from cyanines, squaraines, croconaines and mixtures thereof. Further inorganic IR absorbers are preferably selected from indium tin oxide, antimony tin oxide, lanthanum hexaboride, tungsten bronzes, copper salts etc.

The IR absorbers can be generally used in a concentration of from 10 ppm to 25%, preferably 100 ppm to 10%, depending on the chosen application.

The compounds of formula (I) and IR absorber mixtures are especially suitable for security printing.

Security printing is the field that deals with the printing of items such as currency, passports, tamper-evident labels, stock certificates, postage stamps, identity cards, etc. The main goal of security printing is to prevent forgery, tampering or counterfeiting.

In the field of automated banknote processing, IR-absorption plays an important role. Most of the actually circulating currency carries not only visibly coloured printings, but also specific features which are only detectable in the infrared part of the spectrum. Generally, these IR-features are implemented for use by automatic currency processing equipment, in banking and vending applications (automatic teller machines, automatic vending machines, etc.), in order to recognize a determined currency bill and to verify its authenticity, in particular to discriminate it from replicas made by colour copiers.

Accordingly, the present invention also relates to a method of detecting the authenticity of a security document as defined above, or below, comprising the steps of:

a) measuring an absorbance, reflectance or transmittance spectrum of the security document in the VIS/NIR range of the electromagnetic spectrum; and
b) comparing the spectrum measured under a) and/or information derived therefrom with a corresponding spectrum and/or information of an authentic security element.

All security documents are required to have good stability and durability. In the case of bank notes, these requirements are extreme, as bank notes are subjected to toughest use conditions by the public—they are subjected to material stress by folding, crumpling etc., subjected to abrasion, exposed to weather, exposed to bodily fluids such as perspiration, laundered, dry-cleaned, ironed etc.—and, after having been subjected to this, are expected to be as legible as when they started. Furthermore, it is essential that the documents nevertheless should have a reasonable life time, ideally of some years, despite suffering the afore-mentioned conditions. During this time, the documents, and thus the inks on them (including invisible security markings), should be resistant to fading or colour change. Hence, any ink used in a security printing process should, when cured, be robust, water-resistant, resistant to various chemicals and flexible. Moreover, as certain states are moving away from the use of paper as the substrate for bank notes, the employed printing ink formulations should be useable on plastics as well as paper. The compounds of formula (I) because of its unique application properties are especially suitable for printing ink formulations that are employed for security printing and in particular for bank notes, identity cards, passports, tax stamps, stock certificates, credit cards, labels etc.

In security printing, the IR absorber is added to a printing ink formulation. Suitable printing inks are water-based, oil-based or solvent-based printing inks, based on pigment or dye, for inkjet printing, gravure printing, flexographic printing, screen printing, intaglio printing, offset printing, laser printing or letterpress printing and for use in electrophotography. Printing inks for these printing processes usually comprise solvents, binders, and also various additives, such as plasticizers, antistatic agents or waxes. Printing inks for offset printing, intaglio printing and letterpress printing are usually formulated as high-viscosity paste printing inks, whereas printing inks for inkjet printing, flexographic printing and gravure printing are usually formulated as liquid printing inks with comparatively low viscosity.

In the context of the present invention, the expression "printing ink" also encompasses formulations that in addition to at least one IR absorber of the general formula (I) comprise a colorant. The expression "printing ink" also encompasses printing lacquers that comprise no colorant.

The printing ink formulation for security printing according to the invention preferably comprises a) a compound of formula (I) as defined above,
b) a polymeric binder,
c) a solvent,
d) optionally at least one colorant, and
e) optionally at least one further additive.

Suitable components of printing inks are conventional and are well known to those skilled in the art. Examples of such components are described in "Printing Ink Manual", fourth edition, Leach R. H. et al. (eds.), Van Nostrand Reinhold, Wokingham, (1988). Details of printing inks and their formulation are also disclosed in "Printing Inks"-Ullmann's Encyclopedia of Industrial Chemistry, Sixth Edition, 1999 Electronic Release. A formulation of an IR-absorbing intaglio ink formulation is described in US 20080241492 A1. The disclosure of the afore-mentioned documents is incorporated herein by reference.

The printing ink formulation according to the invention contains in general from 0.0001 to 25% by weight, preferably from 0.001 to 15% by weight, in particular from 0.01 to 5% by weight, based on the total weight of the printing ink formulation, of component a).

The compound of formula (I) is present in the printing ink formulation in dissolved form or in solid form (in a finely divided state).

The printing ink formulation according to the invention contains in general from 5 to 74% by weight, preferably from 10 to 60% by weight, more preferably from 15 to 40% by weight, based on the total weight of the printing ink formulation, of component b).

Suitable polymeric binders b) for the printing ink formulation according to the invention are for example selected from natural resins, phenol resin, phenol-modified resins, alkyd resins, polystyrene homo- and copolymers, terpene resins, silicone resins, polyurethane resins, urea-formaldehyde resins, melamine resins, polyamide resins, polyacrylates, polymethacrylates, chlorinated rubber, vinyl ester resins, acrylic resins, epoxy resins, nitrocellulose, hydrocarbon resins, cellulose acetate, and mixtures thereof.

The printing ink formulation according to the invention can also comprise components that form a polymeric binder by a curing process. Thus, the printing ink formulation according to the invention can also be formulated to be energy-curable, e.g. able to be cured by UV light or EB (electron beam) radiation. In this embodiment, the binder comprises one or more curable monomers and/oligomers. Corresponding formulations are known in the art and can be found in standard textbooks such as the series "Chemistry & Technology of UV & EB Formulation for Coatings, Inks & Paints", published in 7 volumes in 1997-1998 by John Wiley & Sons in association with SITA Technology Limited.

Suitable monomers and oligomers (also referred to as prepolymers) include epoxy acrylates, acrylated oils, urethane acrylates, polyester acrylates, silicone acrylates, acrylated amines, and acrylic saturated resins. Further details and examples are given in "Chemistry & Technology of UV & EB Formulation for Coatings, Inks & Paints", Volume II: Prepolymers & Reactive Diluents, edited by G Webster.

If a curable polymeric binder is employed, it may contain reactive diluents, i.e. monomers which act as a solvent and which upon curing are incorporated into the polymeric binder. Reactive monomers are typically chosen from acrylates or methacrylates, and can be monofunctional or multifunctional. Examples of multifunctional monomers include polyester acrylates or methacrylates, polyol acrylates or methacrylates, and polyether acrylates or methacrylates.

In the case of printing ink formulations to be cured by UV radiation, it is usually necessary to include at least one photoinitiator to initiate the curing reaction of the monomers upon exposure to UV radiation. Examples of useful photoinitiators can be found in standard textbooks such as "Chemistry & Technology of UV & EB Formulation for Coatings, Inks & Paints", Volume III, "Photoinitiators for Free Radical Cationic and Anionic Polymerisation", 2nd edition, by J. V. Crivello & K. Dietliker, edited by G. Bradley and published in 1998 by John Wiley & Sons in association with SITA Technology Limited. It may also be advantageous to include a sensitizer in conjunction with the photoinitiator in order to achieve efficient curing.

The printing ink formulation according to the invention contains in general from 1 to 94.9999% by weight, preferably from 5 to 90% by weight, in particular from 10 to 85% by weight, based on the total weight of the printing ink formulation, of a solvent c).

Suitable solvents are selected from water, organic solvents and mixtures thereof. For the purpose of the invention, reactive monomers which also act as solvents are regarded as part of the afore-mentioned binder component b).

Examples of solvents comprise water; alcohols, e.g. ethanol, 1-propanol, 2-propanol, ethylene glycol, propylene glycol, diethylene glycol and ethoxy propanol; esters, e.g. ethyl acetate, isopropyl acetate, n-propyl acetate and n-butyl acetate; hydrocarbons, e.g. toluene, xylene, mineral oils and vegetable oils, and mixtures thereof.

The printing ink formulation according to the invention may contain an additional colorant d). Preferably, the printing ink formulation contains from 0 to 25% by weight, more preferably from 0.1 to 20% by weight, in particular from 1 to 15% by weight, based on the total weight of the printing ink formulation, of a colorant d).

Suitable colorants d) are selected conventional dyes and in particular conventional pigments. The term "pigment" is used in the context of this invention comprehensively to identify all pigments and fillers, examples being colour pigments, white pigments, and inorganic fillers. These include inorganic white pigments, such as titanium dioxide, preferably in the rutile form, barium sulfate, zinc oxide, zinc sulfide, basic lead carbonate, lithopones (zinc sulfide+barium sulfate), or coloured pigments, examples being iron oxides, bismuth vanadates, lead chromates, lead molybdates, iron blue, Cobalt blue, Cobalt green, Ni-rutile yellow, Cr-rutil yellow, zinc yellow, zinc green, ultramarine, manganese black, antimony black, manganese violet, carbon black, graphite. Besides the inorganic pigments the printing ink formulation of the invention may also comprise organic colour pigments, examples being Monoazo, Disazo, ß-Naphthol, Naphthol AS, Azo pigment Lakes, Benzimidazolone, Metal complex pigments, Isoindolinone, Isoindoline, Phthalocyanine, Quinacridone, Perylene, perinone, Diketopyrrolo-Pyrrol, Thioindigo, Anthraquinone, Anthrapyrimidine, Indanthrone, Flavanthrone, Pyranthrone, Dioxazine, Triarylcarbonium, Quinophthalone. Also suitable are synthetic white pigments with air inclusions to increase the light scattering, such as the Rhopaque® dispersions. Suitable fillers are, for example, aluminosilicates, such as feldspars, silicates, such as kaolin, talc, mica, magnesite, alkaline earth metal carbonates, such as calcium carbonate, in the form for example of calcite or chalk, magnesium carbonate, dolomite, alkaline earth metal sulfates, such as calcium sulfate, silicon dioxide, etc.

The printing ink formulation according to the invention may contain at least one additive e). Preferably, the printing ink formulation contains from 0 to 25% by weight, more preferably from 0.1 to 20% by weight, in particular from 1 to 15% by weight, based on the total weight of the printing ink formulation, of at least one component e).

Suitable additives (component e)) are selected from plasticizers, waxes, siccatives, antistatic agents, chelators, antioxidants, stabilizers, adhesion promoters, surfactants, flow control agents, defoamers, biocides, thickeners, etc. and combinations thereof. These additives serve in particular for fine adjustment of the application-related properties of the printing ink, examples being adhesion, abrasion resistance, drying rate, or slip.

In particular, the printing ink formulation for security printing according to the invention preferably contains a) 0.0001 to 25% by weight of the compound of formula (I), b) 5 to 74% by weight of at least one polymeric binder, c) 1 to 94.9999% by weight of at least one a solvent, d) 0 to 25% by weight of at least one colorant, and e) 0 to 25% by weight of at least one further additive, wherein the sum of components a) to e) adds up to 100%.

The printing ink formulations according to the invention are advantageously prepared in a conventional manner, for example by mixing the individual components. As mentioned earlier, the compound of formula (I) is present in the printing ink formulations in a dissolved or finely divided solid form. Additional colorants may be employed in the printing ink formulation of the invention or in a separate ink formulation. When additional colorants are to be employed in a separate formulation, the time of application of the printing ink formulation according to the invention is usually immaterial. The printing ink formulation according to the invention can for example be applied first and then be overprinted with conventional printing inks. But it is also possible to reverse this sequence or, alternatively, to apply the printing ink formulation according to the invention in a mixture with conventional printing inks. In every case the prints are readable with suitable light sources.

Primers can be applied prior to the printing ink formulation according to the invention. By way of example, the primers are applied in order to improve adhesion to the substrate. It is also possible to apply additional printing lacquers, e.g. in the form of a covering to protect the printed image. Additional printing lacquers may also be applied to serve aesthetic purposes, or serve to control application-related properties. By way of example, suitably formulated additional printing lacquers can be used to influence the roughness of the surface of the substrate, the electrical properties, or the water-vapour-condensation properties. Printing lacquers are usually applied in-line by means of a lacquering system on the printing machine employed for printing the printing ink formulation according to the invention.

The printing ink formulations according to the invention are also suitable for use in multilayer materials. Multilayer materials are e.g. composed of two or more plastics foils, such as polyolefin foils, metal foils, or metallised plastics foils, which are bonded to one another, by way of example, via lamination or with the aid of suitable laminating adhesives. These composites may also comprise other functional layers, such as odour-barrier layers or water-vapour barriers.

The compound of formula (I) and IR absorber mixtures are also especially suitable for laser welding of plastics.

The laser welding is preferably carried out using an ND:YAG laser at 1064 nm or using a diode laser at 980 nm or 940 nm. The concentration of the new crystal form of compound (1) or an IR absorber mixtures is e.g. from 5 to 500 ppm, preferably from 10 to 200 ppm.

In laser welding, plastics components are welded to one another. The plastics components to be fused may have any shape. For example, at least one of the plastics components may be a film.

The compound of formula (I) is suitable for welding transparent at least translucent plastics materials. The employed plastics materials may be colourless or coloured. In principle, the plastics components to be fused may be composed of the same polymer or of different polymers. Preferably, the plastics components employed for laser welding are selected from thermoplastic polymers. However, it is also possible that neither of the plastics components to be fused is composed of thermoplastic; however, a coating of at least one part with a thermoplastic comprising the compound of formula (I) is required.

The plastics components employed for laser welding preferably comprise or consist of at least one polymer selected from polyolefins, polyolefin copolymers, polytetrafluoroethylenes, ethylene-tetrafluoroethylene copolymers, polyvinyl chlorides, polyvinylidene chlorides, polyvinyl alcohols, polyvinyl esters, polyvinyl alkanals, polyvinyl ketals, polyamides, polyimides, polycarbonates, polycarbonate blends, polyesters, polyester blends, poly(meth)acrylates, poly(meth)acrylate-styrene copolymer blends, poly (meth)acrylate-polyvinylidene difluoride blends, polyurethanes, polystyrenes, styrene copolymers, polyethers, polyether ketones and polysulfones and mixtures thereof.

Preference is given to matrix polymers from the group of the polyolefins, polyolefin copolymers, polyvinyl alkanals, polyamides, polycarbonates, polycarbonate-polyester blends, polycarbonate-styrene copolymer blends, polyesters, polyester blends, poly(meth)acrylates, poly(meth)acrylate-styrene copolymer blends, poly(meth)acrylate-polyvinylidene difluoride blends, styrene copolymers and polysulfones and mixtures thereof.

Particularly preferred polymers are transparent or at least translucent. Examples include: polypropylene, polyvinylbutyral, nylon-[6], nylon-[6,6], polycarbonate, polycarbonate-polyethylene terephthalate blends, polycarbonate-polybutylene terephthalate blends, polycarbonate-acrylonitrile/styrene/acrylonitrile copolymer blends, polycarbonate-acrylonitrile/butadiene/styrene copolymer blends, polymethyl methacrylate-acrylonitrile/butadiene/styrene copolymer blends (MABS), polyethylene terephthalate, polybutylene terephthalate, polymethyl methacrylate, impact-modified polymethyl methacrylate, polybutyl acrylate, polymethyl methacrylate-polyvinylidene difluoride blends, acrylonitrile/butadiene/styrene copolymers (ABS), styrene/acrylonitrile copolymers (SAN), polyphenylenesulfone and mixtures comprising 2 or more (e.g. 2, 3, 4, 5) of the afore-mentioned polymers.

Suitable polymer preparations for laser welding comprise

A) a thermoplastic matrix polymer suitable for forming the plastics parts,

B) the compound of formula (I) as defined before,

C) optionally at least one further additive.

Those polymer preparations for laser welding are likewise in accordance with the invention and are suitable for producing fusion-bonded plastics parts with the aid of laser radiation whose wavelength is outside the visible region.

Polymer preparations for laser welding may advantageously be produced by a conventional extrusion or kneading process. The components B), and, if present, C) may be mixed from the outset, in the weight ratio corresponding to the desired end concentration, with the matrix polymer A) (direct compounding), or a distinctly higher concentration of B) and, if present, C) may initially be selected and the concentrate formed (masterbatch) subsequently diluted with further matrix polymer A) in the course of the manufacture of the parts to be fused.

Suitable additives C) are UV stabilizers, antioxidants, processing plasticizers, etc.

In addition, the polymer preparations for laser welding may comprise at least one colorant for establishing a desired hue as additive, especially transparent organic pigments and in particular dyes, for example C.I. Pigment Yellow 109, 110, 128, 138, 139, 150, 151, 147, 180, 183, 185 192 and 196, C.I. Pigment Orange 70, C.I. Pigment Red 122, 149, 178 and 179, 181, 202, 263, C.I. Pigment Violet 19, 23, 37 and 29, C.I. Pigment Blue 15, 15:1, 15:3 and 15:4, 60, C.I. Pigment Green 7 and 36, C.I. Solvent Yellow 14, 21, 93, 130, 133, 145, 163, C.I. Solvent Red 52, 135, 195, 213, 214 and 225, C.I. Solvent Blue 35, 45, 67, 68, 97, 104, 122, 132, C.I. Solvent Violet 13, 46, 49, C.I. Solvent Green 3, 5 and 28, C.I. Solvent Orange 47, 60, 86, 114, and 163, C.I. Solvent Brown 35, 53, and also C.I. Disperse Yellow 54, 87, 201, C.I. Disperse Orange 30, C.I. Disperse Red 60 and C.I. Disperse Violet 57.

A further possible additive group is that of additives which likewise modify the visual appearance, the mechanical properties or else the tactile properties, for example matting agents, such as titanium dioxide, chalk, barium sulfate, zinc sulfide, fillers, such as nanoparticulate silicon dioxide, aluminium hydroxide, clay and other sheet silicates, glass fibers and glass spheres.

The present invention further provides a color converter comprising (i) a compound of formula (I) as defined above;

(ii) a polymeric matrix material selected from a polystyrene, polycarbonate, polyacrylate, polymethylmethacrylate, polymethacrylate, polyvinylpyrrolidone, polyvinyl acetate, polyvinyl chloride, polybutene, silicone, epoxy resin, polyvinyl alcohol, poly(ethylene vinylalcohol)-copolymer, polyacrylonitrile, polyvinylidene chloride, polystyrene acrylonitrile, polybutylene terephthalate, polyethylene terephthalate, a 2,5-furandicarboxylate polyester, polyvinyl butyrate, polyvinyl chloride, polyamides, polyoxymethylenes, polyimides, polyetherimides or mixtures thereof; and (iii) optionally a light scattering agent.

The concentration of the compound of formula (I) as defined above and, if appropriate, of further colorants in the polymer matrix is set as a function of the thickness of the color converter and the type of polymer. If a thin polymer layer is used, the concentration of the compound of formula (I) and, if appropriate the concentration of further colorants, is generally higher than in the case of a thick polymer layer. Preferably, the concentration of the compound of formula (I) according to the present invention is in the range of from 0.001 to 2% by weight, especially 0.001 to 1% by weight, based on the weight of the polymeric matrix material.

In one embodiment of the invention, the color converter does not comprise a light scattering agent.

In another embodiment of the invention, the color converter comprises a light scattering agent. In a preferred embodiment of the invention, the polymeric matrix material comprises scattering agents. Suitable light scattering agents are inorganic white pigments, for example titanium dioxide, barium sulfate, lithopone, zinc oxide, zinc sulfide, calcium carbonate with a mean particle size to DIN 13320 of 0.01 to 10 μm, preferably 0.1 to 1 μm, more preferably 0.15 to 0.4 μm. These light scattering agents are included typically in an amount of 0.01 to 2.0% by weight, preferably 0.05 to 1.0% by weight, more preferably 0.1 to 0.6% by weight, based in each case on the polymer of the layer comprising scattering bodies.

Examples of suitable organic light scattering agents include scattering polymers such as those based on poly (acrylates); poly (alkyl methacrylates), for example poly (methyl methacrylate) (PMMA); poly (tetrafluoroethylene) (PTFE); silicone-based scattering agents, for example hydrolyzed poly(alkyl trialkoxysilanes), and mixtures thereof. The size of these light scattering agents (average diameter-weight average) is usually in the range from 0.5 to 50 μm, preferably 1 to 10 μm. These light scattering agents are typically included in an amount of 1 to 10% by weight, based in each case on the polymer of the layer comprising scattering bodies. Useful light scattering agents are for example a mixture of 3 to 5% by weight of PMMA based scattering agent and 1.5 to 2% by weight of silicone based scattering agent.

Also suitable are light-scattering compositions which contain polymeric particles based on vinyl acrylate with a core/shell morphology in combination with $TiO_2$ as described in EP-A 634 445.

The polymeric matrix material can also comprise at least one further additive selected from an UV absorber, a hindered amine light stabilizer, flame retardant, UV stabilizer, thermal stabilizer, anti-oxidant, plasticizer, antifogging agent, nucleating agent, antistatic agent, filler or a reinforcing material, or combinations thereof.

Hindered amine light stabilizers, UV stabilizers and thermal stabilizers are known to those skilled in the art. Suitable antioxidants or free-radical scavengers are, for example, phenols, especially sterically hindered phenols, such as butylhydroxyanisole (BHA) or butylhydroxytoluene (BHT), or sterically hindered amines (HALS). Stabilizers of this kind are sold, for example, by BASF under the Irganox® trade name. In some cases, antioxidants and free-radical scavengers can be supplemented by secondary stabilizers, such as phosphites or phosphonites, as sold, for example, by BASF under the Irgafos® trade name.

Suitable UV absorbers are, for example, benzotriazoles, such as 2-(2-hydroxyphenyl)-2H-benzotriazole (BTZ), triazines, such as (2-hydroxyphenyl)-s-triazine (HPT), hydroxybenzophenones (BP) or oxalanilides. UV absorbers of this kind are sold, for example, by BASF under the Uvinul® trade name.

The color converter comprising the compound of formula (I) can be part of an agricultural foil, agricultural netting or a greenhouse screen or an illumination device. The color converter may be supported by glass. Likewise it is possible that the agricultural foil, agricultural netting or greenhouse screen consists of the color converter used according to the invention. The color converter according to the present invention can also be part of a near infrared light source.

Thus, a further object of the present invention relates to a near infrared light source, comprising (i) a light source, selected from a blue LED, red LED or white LED; and (ii) a color converter as defined above.

The near infrared light source may be part of a NIR-LED or a near infrared spectrometer.

The invention will be illustrated in detail by the examples.

Examples

General Information

Unless otherwise noted, all chemicals, reagents and solvents were purchased from commercial suppliers and used after appropriate purification. Column chromatography was performed on silica gel (particle size 0.040-0.063 mm) with freshly distilled solvents. $^{1}H$ and $^{13}C$ NMR spectra were recorded on a BrukerAvance HD III 400 or BrukerAvance HD III 600 spectrometer. The $^{13}C$ NMR spectra are broad band proton decoupled. Chemical shifts (δ) are listed in parts per million (ppm) and are reported relative to tetramethylsilane and referenced internally to residual proton solvent resonances or natural abundance carbon resonances. The coupling constants (J) are quoted in Hertz (Hz). MALDI TOF mass spectra were acquired on a Bruker Daltonics autoflex II LRF mass spectrometer. ESI TOF and APCI TOF measurements were carried out on a Bruker Daltonics micOTOF focus mass spectrometer. Melting points were measured on an Olympus BX41 polarisation microscope with a temperature regulator TP84 from Linkam Scientific. The reported values are uncorrected.

Gel Permeations Chromatography (GPC)

Gel permeations chromatography was performed on a Prominence CBM GPC-device with recycling-mode from Shimadzu. Ethanol-stabilized chloroform (HPLC-grade) was used as a solvent.

High-Performance Liquid Chromatography (HPLC)

Semipreparative HPLC was carried out on a JAI LC-9105 HPLC-device from Japan Analytical Industries, while HPLC-grade solvents were used. Semipreparative (Ø=20 mm) Reprosil 100 Chiral-NR chiral columns from Trentec were used.

UV/Vis/NIR Absorption, Emission and Circular Dichroism Spectroscopy

All measurements were carried out using spectroscopic grade solvents. UV/vis/NIR absorption spectra were recorded on a Jasco V670 or V-770-ST spectrometer. Fluorescence steady-state and lifetime measurements were recorded on a FLS980 Edinburgh Instrument fluorescence spectrometer. The quantum yields were determined by using the relative method and oxazine 1 ($Ø_f$=15% in ethanol; used for 7a and 7b) or 125 ($Ø_f$=23% in DMSO, used for 10) as a reference. The lifetime measurements were performed using pulsed laser diodes and determined with the recording of the instrumental response function (IRF). Circular dichroism spectra were recorded on a Jasco J-810 spectrometer.

Synthetic Procedures and Characterization Data

The compounds 1[15], 6b[22], 8a[13], 9[23] and $[Pd_2(dba)_3]\cdot CHCl_3$[24] were synthesized according to the literature procedures.

Compound 2:

A Schlenk-tube was charged with 2.50 g (3.90 mmol, 1.0 equiv) 1, 13.9 g (78.1 mmol, 20.0 equiv) para-tert-butylphenyl boronic acid, 1.35 g (1.17 mmol, 30 mol %) tetrakis (triphenylphosphine)palladium(0) $[Pd(PPh_3)_4]$, 5.67 g (41.0 mmol, 10.5 equiv) $K_2CO_3$ under an inert atmosphere. Subsequently, 5.0 mL toluene, 1.0 mL ethanol and 2.5 mL water was added (all solvents were degassed prior to use). The reaction mixture was cooled to −78° C. and evacuated and backfilled with nitrogen three times. Subsequently, the reaction mixture was heated to 80° C. for four days. After cooling down to room temperature, the reaction mixture was extracted with dichloromethane, the combined organic phases were dried over $MgSO_4$ and the solvent was removed under reduced pressure. The crude product was purified by column chromatography (gradient of dichloromethane/cyclohexane 1:2 to 1:1). The product was dried under high vacuum to give 2.71 g (2.63 mmol, 67%) of compound 2 as a green solid. m.p.: 287° C. $^{1}H$ NMR ($CD_2Cl_2$, 400 MHz, 298 K): δ/ppm=8.42 (s, 4H), 7.17-6.98 (br, 8H), 6.79-6.46 (br, 8H), 4.20 (t, J=7.90 Hz, 4H), 1.80-1.71 (m, 4H), 1.52-1.45 (m, 4H), 1.37 (s, 36H), 1.02 (t, J=7.4, 6H). $^{13}C$ NMR ($CD_2Cl_2$, 151 MHz, 298 K): δ/ppm=164.0, 150.8, 142.1, 138.2, 133.7, 132.3, 131.9, 128.5, 126.3, 122.6, 40.6, 34.8, 31.4, 30.7, 20.8, 14.1. MS (MALDI-TOF, positive mode, DCTB in chloroform): Calculated for $C_{74}H_{74}N_2O_4$: 1030.56; found: 1030.57. HRMS (ESI-TOF, positive mode, acetonitrile/chloroform): Calculated for $C_{74}H_{74}N_2O_4Na$: 1053.5546; found: 1053.5557 $[M+Na]^+$.

Compound 3:

Under an inert atmosphere 1.00 g (970 μmol, 1.0 equiv) 2 was suspended in 50 mL tert butanol. Subsequently, 5.0 mL water and 54.4 g (970 mmol, 1000 equiv) KOH was added and the mixture was heated to 95° C. for 16 h. After cooling down to room temperature, the reaction mixture was poured onto 500 mL cold 10% HCl-solution and the resulting precipitate was collected and washed with water. The residue was dissolved in dichloromethane and washed with water, dried over $MgSO_4$ and the solvent was removed under reduced pressure. The crude product was purified by column chromatography (gradient of cyclohexane/dichloromethane 1:1 to 1:4; due to decomposition on the column, this step should be done fast) to give 689 mg (748 μmol, 77%) of 3 as a dark green solid. m.p.: >350° C. $^{1}H$ NMR ($CD_2Cl_2$, 400 MHz, 298 K): δ/ppm=8.28 (s, 4H), 7.21-7.01 (br, 8H), 6.78-6.43 (m, 8H), 1.37 (s, 36H). $^{13}C$ NMR ($CD_2Cl_2$, 101 MHz, 298 K): δ/ppm=160.7, 151.6, 143.0, 137.3, 135.8, 133.4, 132.4, 128.5, 128.4, 125.5, 118.8, 34.9, 31.3. MS (MALDI-TOF, negative mode, DCTB in chloroform): Calculated for $C_{64}H_{56}O_6$: 920.41; found: 920.45. HRMS (ESI-TOF, positive mode, acetonitrile/chloroform): Calculated for $C_{64}H_{56}O_6Na$: 943.3975; found: 943.3949 $[M+Na]^+$.

Compound 4a and 4b:

To a suspension of 250.0 mg (271 μmol, 1.0 equiv) 3 in 25 mL water an aqueous 1 M NaOH-solution (1.63 mL, 1.63 mmol, 6.0 eq) was added and the mixture heated to 85° C. Subsequently, THF was added carefully in small portions until a clear solution appeared (ca. 25 mL) and the reaction mixture was further heated to 85° C. for 20 minutes. Afterwards, 556 μL (10.9 mmol, 1.73 g, 40.0 equiv, 3.12 g/mL) bromine was added in one portion and the mixture was heated to 85° C. for 16 h. After cooling down to room temperature, the reaction mixture was poured onto 100 mL 10% HCl-solution, filtered and washed with water. The precipitation was dissolved in dichloromethane, washed with water, dried over $MgSO_4$ and the solvent was removed under reduced pressure. The crude product was purified by column chromatography (dichloromethane/cyclohexane 2:3) to yield 4a (68.7 mg, 68.1 μmol, 25%, bluish green solid) and 4b (111.2 mg, 101 μmol, 37%, red solid). Characterization data of 4a: m.p.: >350° C. $^1H$ NMR ($CD_2Cl_2$, 400 MHz, 298 K): δ/ppm=8.21 (s, 2H), 7.72 (s, 2H), 7.12-7.01 (m, 8H), 6.70-6.30 (br, 8H), 1.37 (s, 18H), 1.35 (s, 18H). $^{13}C$ NMR ($CD_2Cl_2$, 101 MHz, 298 K): δ/ppm=161.2, 151.1, 150.8, 142.8, 140.9, 138.7, 137.5, 137.2, 137.1, 135.5, 135.2, 132.3, 128.7, 128.2, 127.9, 126.6, 122.3, 117.0, 34.8, 34.8, 31.4, 31.4. MS (MALDI-TOF, positive mode, DCTB in chloroform): Calculated for $C_{62}H_{56}Br_2O_3$: 1008.26; found: 1008.32. HRMS (ESI-TOF, positive mode, acetonitrile/chloroform): Calculated for $C_{62}H_{56}Br_2O_3Na$: 1029.2494; found: 1029.2488 $[M+Na]^+$. Characterization data of 4b: m.p.: 272° C. $^1H$ NMR ($CD_2Cl_2$, 400 MHz, 298 K): δ/ppm=7.63 (s, 4H), 7.06-7.01 (m, 8H), 6.49-6.36 (br, 8H), 1.35 (s, 36H). $^{13}C$ NMR ($CD_2Cl_2$, 101 MHz, 298 K): δ/ppm=150.3, 140.8, 138.1, 137.6, 137.3, 128.6, 128.0, 127.2, 126.1, 119.5, 34.8, 31.4. MS (MALDI-TOF, positive mode, DCTB in chloroform): Calculated for $C_{60}H_{56}Br_4$: 1096.11; found: 1096.17. HRMS (APCI, positive mode, acetonitrile/chloroform): Calculated for $C_{60}H_{56}Br_4$: 1092.1116; found: 1092.1110.

Compound 5:

A mixture of 25.0 mg (24.8 μmol, 1.0 equiv) 4a and 43.9 mg (46.7 μl, 247.8 μmol, 10.0 equiv) 2,6-diisopropyl aniline in 0.25 mL acetic acid and 0.5 mL N-methyl-2-pyrrolidone was heated to 110° C. for 24 h. After cooling down to room temperature, the reaction mixture was poured onto water, extracted with dichloromethane, the combined organic phases dried over $MgSO_4$ and the solvent removed under reduced pressure. The crude product was further purified by column chromatography (cyclohexane/dichloromethane 1:1) to yield 14.0 mg (12.0 μmol, 48%) of compound 5 as a dark purple solid. m.p.: 286-290° C. $^1H$ NMR ($CD_2Cl_2$, 400 MHz, 298 K): 6/ppm=8.25 (s, 2H), 7.71 (s, 2H), 7.51 (t, J=7.8 Hz, 1H), 7.36 (d, J=7.8 Hz, 2H), 7.11-7.05 (m, 8H), 6.80-6.30 (m, 8H), 2.86 (sep, J=6.9 Hz, 2H), 1.36 (s, 36H), 1.22 (d, J=6.9 Hz, 6H), 1.13 (d, J=6.9 Hz, 6H). $^{13}C$ NMR ($CD_2Cl_2$, 101 MHz, 298 K): 6/ppm=164.6, 150.8, 150.5, 146.6, 142.6, 140.9, 138.9, 138.2, 137.6, 137.2, 134.0, 133.7, 132.4, 132.1, 129.7, 128.6, 128.4, 127.9, 127.2, 126.7, 124.4, 121.7, 121.0, 34.8, 34.8, 31.4, 31.4, 24.2, 24.1. MS (MALDI-TOF, negative mode, DCTB in chloroform): Calculated for $C_{74}H_{73}Br_2NO_2$: 1167.40; found: 1167.45. HRMS (ESI-TOF, positive mode, acetonitrile/chloroform): Calculated for $C_{74}H_{73}Br_2NO_2Na$: 1188.3906; found: 1188.3874 $[M+Na]^+$.

Compound 7a (Example 1):

Starting from 8a:

A Schlenk-tube was charged with 25.0 mg (33.6 μmol, 1.0 equiv) 8a, 120 mg (672 μmol, 20.0 equiv) para-tert-butylphenyl boronic acid, 11.7 mg (10.1 μmol, 30 mol %) tetrakis(triphenylphosphine)palladium(0) $[Pd(PPh_3)_4]$, 45.3 mg (328 μmol, 9.75 equiv) $K_2CO_3$ under an inert atmosphere. Subsequently, 2.5 mL toluene, 0.5 mL ethanol and 1.25 mL water was added (all solvents were degassed prior to use). The reaction mixture was cooled to −78° C. and evacuated and backfilled with nitrogen three times. Subsequently, the reaction mixture was heated to 80° C. for 16 h. After cooling down to room temperature, the reaction mixture was extracted with dichloromethane, the combined organic phases were dried over $MgSO_4$ and the solvent was removed under reduced pressure. The crude product was purified by column chromatography (dichloromethane/cyclohexane 1:1), followed by GPC (chloroform). The product was dried under high vacuum to give 2.4 mg (2.12 mmol, 6%) of compound 7a as a dark-green solid.

Starting from 5:

A Schlenk-tube was charged with 3.9 mg (15.4 μmol, 1.0 equiv) 6a, 19.7 mg (16.9 μmol, 1.1 equiv) 5, 1.6 mg (1.57 μmol, 10 mol %) tris(dibenzylideneacetone)dipalladium(0)-chloroform adduct $[Pd_2(dba)_3]\cdot CHCl_3$, 2.3 mg (6.14 μmol, 40 mol %) tricyclohexylphosphine tetrafluoroborate $PCy_3\cdot HBF_4$, 15.0 mg (46.0 μmol, 3.0 equiv) $Cs_2CO_3$ and 0.47 mL 1-chloronaphthalene as a solvent under an inert atmosphere at room temperature and heated to 160° C. for 16 h. After cooling down to room temperature, the reaction mixture was filtrated with cyclohexane over a pad of silica gel to remove 1-chloronaphthalene and the crude product was eluated with dichloromethane. The crude product was purified by column chromatography (gradient of dichloromethane/cyclohexane 1:1 to 1:0), followed by GPC (chloroform). The product was dried under high vacuum to give 3.3 mg (2.91 μmol, 19%) of compound 7a as a dark-green solid.

m.p.: >350° C. $^1H$ NMR ($CD_2Cl_2$, 400 MHz, 298 K): δ/ppm=8.40 (d, J=7.9 Hz, 2H), 8.26 (s, 2H), 8.09 (s, 2H), 7.87 (d, J=7.9 Hz, 2H), 7.62 (t, J=7.9 Hz, 2H), 7.51 (t, J=7.9 Hz, 1H), 7.37 (d, J=7.9 Hz, 2H), 7.22-6.50 (m, 16H), 2.87 (sep, J=6.9 Hz, 2H), 1.41 (s, 18H), 1.36 (s, 18H), 1.23 (d, J=6.9 Hz, 6H), 1.12 (d, J=6.9 Hz, 6H). $^{13}C$ NMR ($CD_2Cl_2$, 101 MHz, 298 K): δ/ppm=164.8, 150.3, 150.0, 146.7, 143.4, 140.3, 139.7, 139.2, 134.9, 134.4, 134.2, 133.9, 133.2, 132.5, 132.3, 130.6, 129.6, 129.6, 128.6, 128.2, 128.2, 127.3, 127.1, 126.6, 126.6, 124.9, 124.4, 122.5, 120.2, 34.8, 34.8, 31.5, 31.4, 30.1, 29.4, 24.3, 24.1. UV/vis ($CH_2Cl_2$): $\lambda_{max}$/nm ($\varepsilon/M^{-1}cm^{-1}$)=679 (19800). Fluorescence ($CH_2Cl_2$, $\lambda_{ex}$=590 nm): $\lambda_{max}$/nm ($Ø_f$/%)=768 (1.4±0.1). MS (MALDI-TOF, positive mode, DCTB in chloroform): Calculated for $C_{84}H_{79}NO_2$: 1133.61; found: 1133.61. HRMS (ESI-TOF, positive mode, acetonitrile/chloroform): Calculated for $C_{84}H_{79}NO_2K$: 1172.5748.2212; found: 1172.5747 $[M+K]^+$.

Compound 7b (Example 2):

A Schlenk-tube was charged with 6.0 mg (16.0 μmol, 1.0 equiv) 6b, 20.5 mg (17.6 μmol, 1.1 equiv) 5, 1.7 mg (1.60 μmol, 10 mol %) tris(dibenzylideneacetone)dipalladium(0)-chloroform adduct $[Pd_2(dba)_3]\cdot CHCl_3$, 2.4 mg (6.38 μmol, 40 mol %) tricyclohexylphosphine tetrafluoroborate $PCy_3\cdot HBF_4$, 16.0 mg (47.8 μmol, 3.0 equiv) $Cs_2CO_3$ and 0.48 mL 1-chloronaphthalene as a solvent under an inert atmosphere at room temperature and heated to 160° C. for 16 h. After cooling down to room temperature, the reaction mixture was filtrated with cyclohexane over a pad of silica gel to remove 1-chloronaphthalene and the crude product was eluated with dichloromethane/cyclohexane 1:1-mixture. The crude product was purified by GPC (chloroform), followed by preparative thin layer chromatography (dichloromethane/cyclohexane 2:3). The product was dried under high vacuum to give 3.0 mg (2.39 μmol, 15%) of compound 7b as a green solid. m.p.: >350° C. $^1H$ NMR ($CD_2Cl_2$, 400 MHz, 298 K): δ/ppm=8.43 (s, 2H), 8.32-8.20 (m, 4H), 7.99-7.81 (m, 6H), 7.51 (t, J=7.8 Hz, 1H), 7.37 (d, J=7.8 Hz, 2H), 7.42-6.59 (m, 162.89 (qui, J=6.9 Hz, 2H), 1.42 (s, 18H), 1.29-1.20 (m, 24H), 1.17-1.10 (m, 6H). $^{13}C$ NMR ($CD_2Cl_2$, 101 MHz, 298 K): δ/ppm=164.7, 150.5, 146.7, 140.7, 139.0, 136.8, 136.4, 134.7, 134.1, 133.6, 132.3, 132.1, 129.6, 1287, 128.3, 128.1, 127.7, 124.4, 120.6, 34.9, 31.5, 30.1, 29.4, 24.3, 24.1. UV/vis ($CH_2Cl_2$): $\lambda_{max}$/nm ($\varepsilon/M^{-1}cm^{-1}$)=682 (14300). Fluorescence ($CH_2Cl_2$, $\lambda_{ex}$=600 nm): $\lambda_{max}$/nm ($Ø_f$/%)=786 (4.8±0.1). MS (MALDI-TOF, positive mode, DCTB in chloroform): Calculated for $C_{94}H_{81}NO_2$: 1256.63; found: 1256.64. HRMS (ESI-TOF, positive mode, acetonitrile/chloroform): Calculated for $C_{94}H_{81}NO_2Na$: 1278.6165; found: 1278.6130 $[M+Na]^+$.

Compound 10a (Example 3):

A Schlenk-tube was charged with 15.0 mg (13.5 μmol, 1.0 equiv) 4b, 14.4 mg (29.7 μmol, 2.2 equiv) 9, 2.8 mg (2.70 μmol, 20 mol %) tris(dibenzylideneacetone)dipalladium(0)-chloroform adduct $[Pd_2(dba)_3]\cdot CHCl_3$, 4.0 mg (10.8 μmol, 80 mol %) tricyclohexylphosphine tetrafluoroborate $PCy_3\cdot HBF_4$, 26.4 mg (81.0 μmol, 6.0 equiv) $Cs_2CO_3$ and 0.40 mL 1-chloronaphthalene as a solvent under an inert atmosphere at room temperature and heated to 160° C. for 20 h. After cooling down to room temperature, the reaction mixture was filtrated with cyclohexane over a pad of silica gel to remove 1-chloronaphthalene and the crude product was eluated with dichloromethane. The crude product was purified by column chromatography (gradient of dichloromethane/cyclohexane 1:1 to 1:0), followed by GPC (chloroform) and preparative thin layer chromatography (dichloromethane/n-hexane 2:1). The product was dried under high vacuum to give 3.5 mg (2.35 μmol, 18%) of compound 10a as a light-green solid. m.p.: >350° C. $^1$H NMR ($CD_2Cl_2$, 400 MHz, 298 K): δ/ppm=8.70 (d, J=8.2 Hz, 4H), 8.63 (d, J=8.2 Hz, 4H), 8.35 (s, 4H), 7.52 (t, J=7.8 Hz, 2H), 7.37 (d, J=7.8 Hz, 4H), 7.22-7.07 (br, 8H), 6.92-6.60 (br, 8H), 2.78 (qui, J=6.8 Hz, 4H), 1.41 (s, 36H)~~, 1.18~~-1.14 (m, 24$^{13}$C NMR ($CD_2Cl_2$, 151 MHz, 298 K): δ/ppm=164.4, 150.5, 146.6, 142.2, 139.4, 137.3, 133.8, 132.1, 131.1, 130.3, 129.7, 129.1, 128.5, 127.6, 127.0, 125.7, 124.4, 121.4, 121.4, 34.8, 31.5, 30.1, 24.1. UV/vis ($CH_2Cl_2$): $\lambda_{max}$/nm (ε/$M^{-1}cm^{-1}$)= 811 (67000). Fluorescence ($CH_2Cl_2$, $\lambda_{ex}$=790 nm): $\lambda_{max}$/nm ($Ø_f$/%)=884 (1.3±0.1). MS (MALDI-TOF, positive mode, DCTB in chloroform): Calculated for $C_{108}H_{98}N_2O_4$: 1487.76; found: 1487.76. HRMS (ESI-TOF, positive mode, acetonitrile/chloroform): Calculated for $C_{108}H_{98}N_2O_4$: 1486.7527; found: 1486.7517 $[M]^+$.

The invention claimed is:

1. A compound of the formula (I)

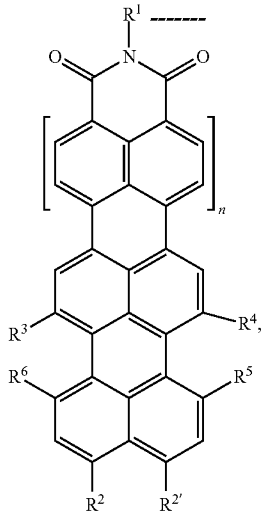

wherein n is 0 or 1

$R^1$ is selected from the group consisting of hydrogen, $C_1$-$C_{24}$-alkyl, $C_1$-$C_{24}$-haloalkyl, $C_3$-$C_{24}$- cycloalkyl, $C_6$-$C_{10}$-aryl and $C_6$-$C_{10}$-aryl-$C_1$-$C_{10}$-alkylene, where the rings of cycloalkyl, aryl, and aryl-alkylene in the three last-mentioned radicals are unsubstituted or substituted with one or more substituents $R^7$, and where $C_1$-$C_{24}$-alkyl, $C_1$-$C_{24}$-haloalkyl and the alkylene moiety of $C_6$-$C_{10}$-aryl-$C_1$-$C_{10}$-alkylene may be interrupted by one or more heteroatoms or heteroatomic groups selected from O, S and $NR^8$;

$R^3$, $R^4$, $R^5$ and $R^6$, independently of each other, are selected from $C_6$-$C_{10}$-aryloxy, $C_2$-$C_{10}$-heteroaryl or $C_6$-$C_{10}$-aryl, wherein $C_6$-$C_{10}$-aryloxy is substituted by one or more identical or different substituents $R^7$; $C_2$-$C_{10}$-heteroaryl is unsubstituted or substituted by one or more identical or different substituents $R^7$ and $C_6$-$C_{10}$-aryl is substituted by one or more identical or different substituents $R^7$ $R^2$ and $R^{2'}$ together form a group of formula (II)

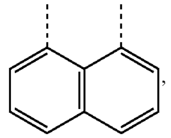

represents the bond to the rylene basic skeleton, the group of formula (II) is unsubstituted or substituted with one or more substituents $R^7$, or the group of formula (II) may be part of an annulated ring system, which is unsubstituted or substituted with one or more substituents $R^7$, or in case of the group of formula (II)

two substituents $R^7$ may form a group

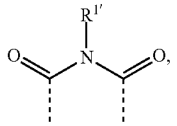

wherein represents the bond to the group of formula (II), $R^{1'}$ is selected from the group consisting of hydrogen, $C_1$-$C_{24}$-alkyl, $C_1$-$C_{24}$-haloalkyl, $C_3$-$C_{24}$-cycloalkyl, $C_6$-$C_{10}$-aryl and $C_6$-$C_{10}$-aryl-$C_1$-$C_{10}$-alkylene, where the rings of cycloalkyl, aryl, and aryl-alkylene in the three last-mentioned radicals are unsubstituted or substituted with one or more substituents $R^7$, and where $C_1$-$C_{24}$- alkyl, $C_1$-$C_{24}$-haloalkyl and the alkylene moiety of $C_6$-$C_{10}$-aryl-$C_1$-$C_{10}$-alkylene may be interrupted by one or more heteroatoms or heteroatomic groups selected from O, S and $NR^8$;

each $R^7$ is selected from $C_1$-$C_{24}$-alkyl, $C_1$-$C_{24}$-fluoroalkyl, $C_1$-$C_{24}$-alkoxy, fluorine, chlorine or bromine;

$R^8$ is hydrogen, $C_1$-$C_{20}$-alkyl, $C_3$-$C_{24}$-cycloalkyl, heterocycloalkyl, hetaryl or $C_6$-$C_{10}$-aryl.

2. The compound according to claim 1, wherein $R^3$, $R^4$, $R^5$ and $R^6$, independently of each other, are selected from phenyl, phenoxy, thienyl, pyridinyl, quinolinyl and isoquinolinyl, which are optionally substituted by one, two or three substituents $R^7$; 1-naphthyl and 2-naphthyl, which are optionally substituted by one, two or three substituents $R^7$.

3. The compound according to claim 1, wherein $R^3$, $R^4$, $R^5$ and $R^6$, independently of each other, are selected from phenoxy, which is substituted by one, two or three substituents $R^7$;

phenyl, which is substituted by one, two or three substituents $R^7$.

4. The compound according to claim 1, wherein $R^1$ and $R^{1'}$, independently of each other, are selected from the group consisting of linear $C_1$-$C_{24}$-alkyl, branched $C_3$-$C_{24}$-alkyl, $C_5$-$C_8$- cycloalkyl, phenyl and phenyl-$C_1$-$C_{10}$-alkylene, where the rings of cycloalkyl, phenyl and phenyl-alkylene in the three last-mentioned radicals are unsubstituted or substituted by 1, 2 or 3 identical or different substituents $R^7$.

5. The compound according to claim 1, which is a compound of formula (Ia)

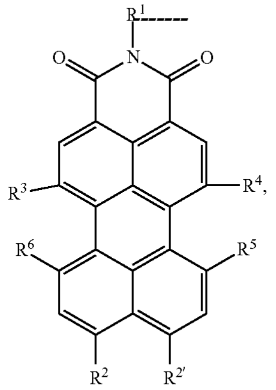

wherein $R^1$ is selected from $C_4$-$C_{20}$-alkyl, $C_5$-$C_8$-cycloalkyl or phenyl, wherein the two last-mentioned substituents are substituted by one, two or three $C_1$-$C_6$-alkyl substituents;

$R^3$, $R^4$, $R^5$ and $R^6$ have the same meaning and are selected from the group consisting of phenyl and phenoxy; which are substituted by one, two or three substituents $R^7$, wherein $R^7$ is $C_1$-$C_{12}$-alkyl; and $R^2$ and $R^{2'}$ together form a group of the formula

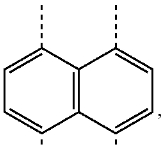, 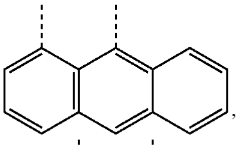,

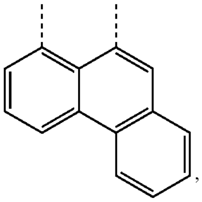, 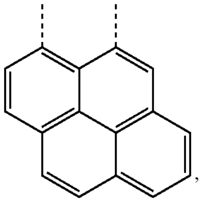,

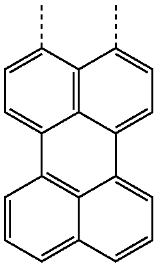, 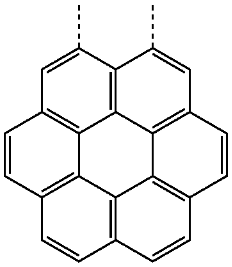, or

-continued

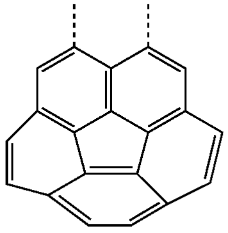, wherein represents the bond to the rylene basic skeleton.

6. The compound according to claim 1, which is a compound of the formula (Ib)

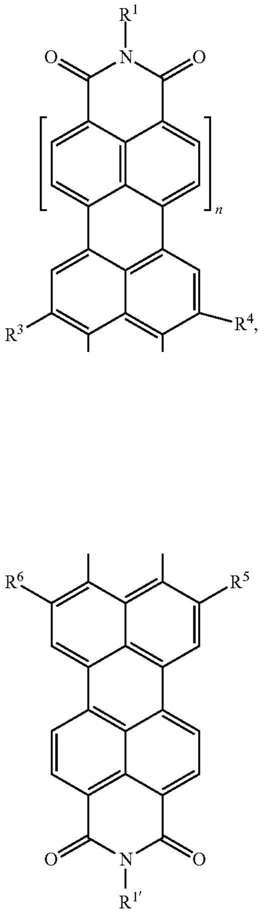

wherein n is 0, or 1

$R^1$ and $R^{1'}$ have the same meaning and are selected from $C_4$-$C_{20}$-alkyl, $C_5$-$C_8$-cycloalkyl or phenyl, wherein the two last-mentioned substituents are substituted by one, two or three $C_1$-$C_6$-alkyl substituents;

$R^3$, $R^4$, $R^5$ and $R^6$ have the same meaning and are selected from the group consisting of phenyl and phenoxy; which are substituted by one, two or three substituents $R^7$.

7. The compound according to claim 1, which is a compound of the formula
(7′)
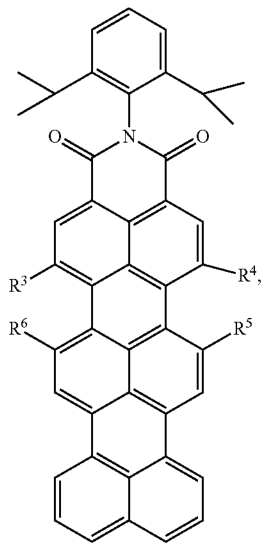
(7″)
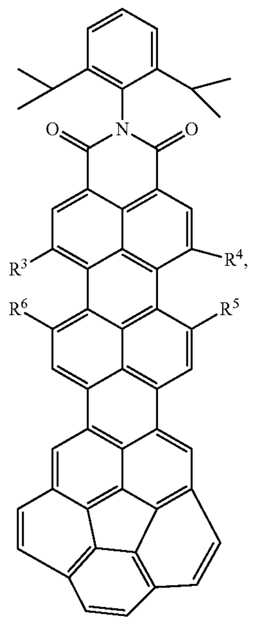
or
(10)
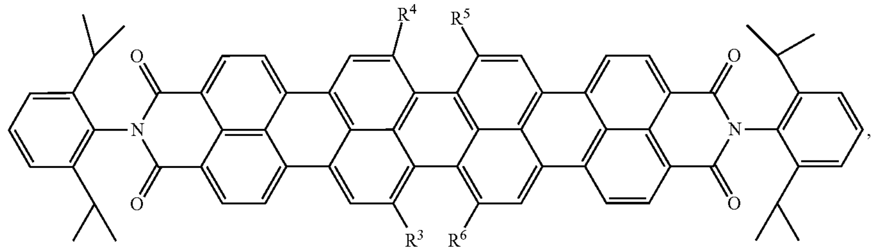
, wherein $R^3$, $R^4$, $R^5$ and $R^6$ are the same and are a group

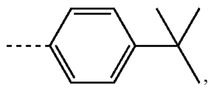

or

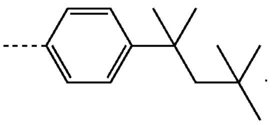

8. A color converter comprising (i) a compound of formula (I) as defined in claim 1;

(ii) a polymeric matrix material selected from a polystyrene, polycarbonate, polyacrylate, polymethylmethacrylate, polymethacrylate, polyvinylpyrrolidone, polyvinyl acetate, polyvinyl chloride, polybutene, silicone, epoxy resin, polyvinyl alcohol, poly (ethylene vinylalcohol)-copolymer, polyacrylonitrile, polyvinylidene chloride, polystyrene acrylonitrile, polybutylene terephthalate, polyethylene terephthalate, a 2,5-furandicarboxylate polyester, polyvinyl butyrate, polyvinyl chloride, polyamides, polyoxymethylenes, polyimides, polyetherimides or mixtures thereof; and iii) optionally a light scattering agent.

9. A near infrared light source, comprising (i) a light source, selected from the group consisting of a blue LED, red LED and white LED; and (ii) a color converter as defined in claim 8.

10. A process for the preparation of a compound of formula (I)

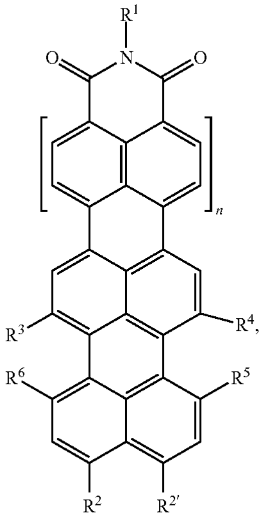

comprising i) reacting a compound of formula (VI)

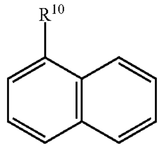

with a compound of formula (V)

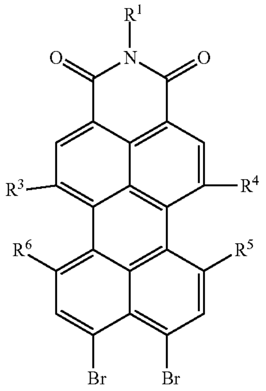

in a solvent and in the presence of a catalyst; or ii) reacting a compound of formula (VI')

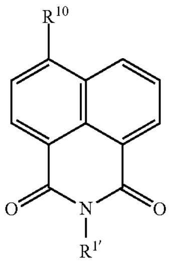

with a compound of formula (IV)

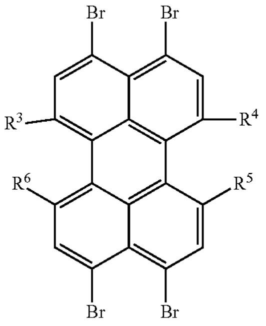

in a solvent and in the presence of a catalyst, wherein $R^{10}$ is —$B(OH)_2$, —$B(OY^1)_2$,

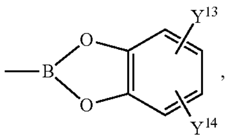

, or

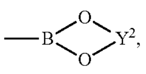

wherein $Y^1$ is independently in each occurrence a $C_1$-$C_{10}$ alkyl group and $Y^2$ is independently in each occurrence a $C_2$-$C_{10}$ alkylene group and $Y^{13}$ and $Y^{14}$ are independently of each other hydrogen, or a $C_1$-$C_{10}$ alkyl group; and n; $R^1$, $R^{1'}$; $R^3$, $R^4$, $R^5$; $R^6$; $R^2$ and $R^{2'}$ are defined in claim 1.

* * * * *